United States Patent [19]

Kurotaki et al.

[11] Patent Number: 5,166,403
[45] Date of Patent: Nov. 24, 1992

[54] AMINE DERIVATIVES AND PROCESS FOR PRODUCING THE SAME

[75] Inventors: Ayako Kurotaki; Shuichi Naijoh; Kimie Nagai; Koro Shirane; Chozo Inoue, all of Tokyo, Japan

[73] Assignee: Showa Denko K.K., Tokyo, Japan

[21] Appl. No.: 640,753

[22] Filed: Jan. 14, 1991

[30] Foreign Application Priority Data

Mar. 29, 1990 [JP] Japan .................................. 2-81975
Mar. 30, 1990 [JP] Japan .................................. 2-86948
Jun. 6, 1990 [JP] Japan .................................. 2-149487

[51] Int. Cl.$^5$ .............................................. C07C 69/76
[52] U.S. Cl. .......................................... 560/59; 560/66; 560/84; 560/85; 560/125; 252/299.1
[58] Field of Search ................. 560/59, 66, 85, 125; 252/299.1

[56] References Cited

FOREIGN PATENT DOCUMENTS 63-2961 1/1988 Japan .
2-53756 2/1990 Japan .

OTHER PUBLICATIONS

Y. Aihara et al, "Synthesis and Properties of Ferroelectric Liquid Crystal Having Isonipecotic Acid", Liquid Crystals and Ordered Fluids, vol. 4, 1984, pp. 50–51.
K. Sharp, "Ferroelectric Liquid Crystals. Material Properties and Applications", Mol. Cryst. Liq. Cryst., 1988, vol. 165, pp. 439–509.
J. W. Goody et al, "Some Novel Ferroelectric Smectic Liquid Crystals", Bell Laboratories, pp. 1–32.

Primary Examiner—Paul J. Killos
Attorney, Agent, or Firm—Sughrue, Mion, Zinn, Macpeak & Seas

[57] ABSTRACT

An amine derivative having a liquid crystal property over a wide temperature range and a process for production thereof are disclosed, the amine derivative being represented by formula (I)

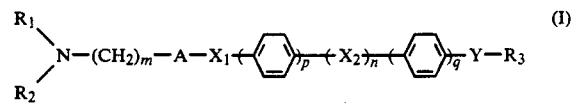

wherein A represents

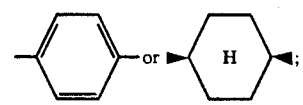

$X_1$ and $X_2$, which may be the same or different, each represents

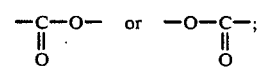

Y represents —O— or

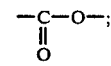

$R_1$ and $R_3$, which may be the same or different, each represents a straight chain or branched chain alkyl group having 1 to 18 carbon atoms; $R_2$ represents a hydrogen atom or a methyl group; m and n each represents 0 or 1; and p and q each represents 1 or 2, provided that p and q are 1 when n is 0, and p and q are not 2 at the same time when n is 1.

11 Claims, 6 Drawing Sheets

Et, Bzl = See FIG. 3 and 5

AMINE DERIVATIVES AND PROCESS FOR PRODUCING THE SAME

FIELD OF THE INVENTION

This invention provides a novel compound showing a liquid crystal property and a process of producing the compound. Furthermore, the invention provides a liquid crystal element using the compound.

The compound provided by the invention has a liquid crystal property and can be used as a thermal writing liquid crystal element and a liquid crystal element for display.

BACKGROUND OF THE INVENTION

In the materials known as liquid crystal compounds, a smectic liquid crystal or a cholesteric liquid crystal exhibiting a transparent liquid crystal texture causes a phenomenon that when the thin layer of the liquid crystal is locally heated and suddenly cooled, the portions are changed into an opaque liquid crystal texture scattering light. This phenomenon is known as a thermo-optical effect of liquid crystals. Various liquid crystal elements for writing information systems by applying a localized temperature change to the liquid crystal cell to opacity portions thereof by utilizing the above-described phenomenon have been proposed.

A material used for thermal writing liquid crystal elements must be stable to moisture, air, and light, and further must have an adequate phase transition temperature.

The term "adequate phase transition temperature" as used herein means a sufficiently wide temperature range including room temperature, under which thermal writing is possible at room temperature and where the storage temperature is not influenced, and it is desired that the liquid crystal is not transformed into other liquid crystal phase than a smectic phase or a cholesteric phase within that temperature range.

A Schiff's base series liquid crystal material shown by the following formula

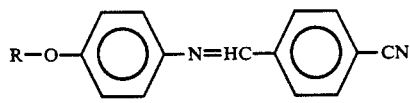

(wherein R represents an alkyl group), which is generally used as a light valve element used for a projection type display system tends to be hydrolyzed whereby the material has a short life time and is unreliable due to low humidity resistance.

Also, as chemically stable compounds, a compound shown by the formula

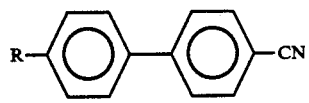

(wherein R represents an alkyl group) is reported but this compound has an insufficient liquid crystal temperature range.

Also, various compounds are known as liquid crystal compounds and these compounds are called nematic liquid crystals. These nematic liquid crystals are the main compound or composition being used in liquid crystal displays at the present time. However, one of the disadvantages of these compounds is that the response speed is slow and a response speed of on the order of a few milliseconds only is obtained. Hence it has been said that the use of such a compound has approached the limit for large-scale displays.

To correct the above-described disadvantage of conventional liquid crystal display elements, the use of a bistable liquid crystal is proposed in JP-A-56-107216 (the term "JP-A" as used herein means an "unexamined published Japanese patent application"). A bistable liquid crystal is called a ferroelectric liquid crystal and it is being watched with keen interest since a fast response and memory are possible by using this type of liquid crystal. In particular, practiced uses of this type of liquid crystal have been actively investigated and the development of a ferroelectric liquid crystal material for practical use has become urgently needed.

In general, a ferroelectric liquid crystal is a compound having an optically active site. The characteristics thereof are achieved by a series of smectic phases having a molecular orientation so that the long axis of the molecule is tilted from the normal direction of the layer. Of these smectic phases, a chiral-smectic C (hereinafter, referred to as Sc*) phase is considered the most promising for practical use due to the relatively low voltage requirements thereof for operation.

Since a ferroelectric liquid crystal has a very fast response speed due to the spontaneous polarization thereof and also can realize a bistable state with memory capabilities and further has excellent view field, the ferroelectric liquid crystal is suitable as a material for a large capacity and large picture size display.

Examples of such ferroelectric liquid crystals include 4-(4'-n-decyloxybenzylideneamino)cinnamic acid 2-methylbutyl ester (hereinafter referred to as DOBAMBC) as described in *J. Physique*, 36, L-69 (1975).

DOBAMBC has a disadvantage in terms of chemical stability since it contains a Schiff's base in the structure. Thus, various physically and chemically stable compounds have been investigated as materials for ferroelectric liquid crystals. At present, 2-methylbutyl 4-(4'-n-alkyloxybenzoyloxy)benzoate (hereinafter, referred to as CN) and other similar ester series compounds have been mainly investigated. However, since CN and other similar ester series compounds do not exhibit a Sc* phase or, even when these compounds show the Sc* phase, the temperature range within which the Sc* phase is exhibited is narrow. Also these compounds are monotropic liquid crystal each exhibiting different phase series between heating the liquid crystal and cooling the liquid crystal. Thus, few compounds are capable of being practically used as described in *Liquid Crystals and Ordered Fluids*, 4 (1984).

On the other hand, the introduction of a heterocyclic ring (e.g., a pyridine ring, a pyrimidine ring, etc.) or the introduction of a cyclohexane ring into a molecule of such compounds is generally used to shift its liquid crystal phase temperature range to a temperature range including room temperature. However, the synthesis method thereof is complicated.

In particular, since the introduction of a cyclohexane ring for improving the liquid crystal property has the problems that the smectic property is lost by the introduction of the cyclohexane ring and the synthesis requires the cis isomer of 1,4-di-substituted cyclohexane and the trans isomer thereof to be separated from a mixture thereof, sufficient investigation of these compounds has not been made.

Various ferroelectric liquid crystal compounds containing a hetero atom are known and examples include ferroelectric liquid crystal compounds containing a nitrogen atom, compounds containing a nitrogen atom in a heterocyclic ring such as a pyrimidine ring as described above (JP-A-61-22072, JP-A-61-24576, and JP-A-61-129170) and compounds containing a Schiff's base as a linking group, such as DOBAMBC, are known.

Of the compounds containing a nitrogen atom as a linking group, compounds containing a Schiff's base have chemical stability problems as described above. Also, the compounds containing an amide bond are not effective since they have a high melting point and tend not to show a liquid crystal property.

Examples of compounds containing a nitrogen atom in the form of an amine such as those containing an aromatic secondary amine are disclosed in JP-A-63-2961 and JP-A-2-53756. However, the temperature ranges of these compounds showing the liquid crystal property are all narrow. Thus, these compounds have not yet been practically used.

SUMMARY OF THE INVENTION

A first object of this invention is to provide a novel amine derivative which is chemically stable and shows the liquid crystal property over a wide temperature range.

A second object of this invention is to provide a process for producing a novel liquid crystal compound using an N-substituted amine derivative where the kind of an alkyl group can be easily changed as an intermediate.

A third object of this invention is to provide a liquid crystal compound where the kind and length of an alkyl group and the kind of an ester group can be easily varied and the kind and temperature range of the liquid crystal phase realized in a liquid crystal state can be controlled.

The synthesis of a compound showing a stable liquid crystal property over a wide temperature range has now been achieved by esterification reaction of an N-substituted amine derivative as an intermediate and a biphenyl derivative or a phenylbenzoate derivative.

It has been discovered that the aforesaid objects can be attained by an amine derivative represented by following formula (I):

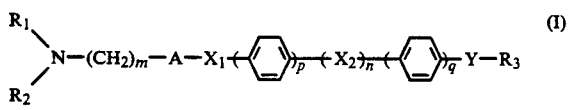

wherein A represents

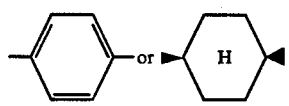

(showing a trans configuration); $X_1$ and $X_2$ each represents

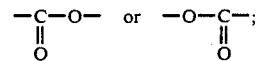

Y represents —O— or

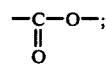

$R_1$ and $R_3$ each represents a straight chain or branched alkyl group having 1 to 18 carbon atoms; $R_2$ represents a hydrogen atom or a methyl group; m and n each represents 0 or 1; and p and q each represents 1 or 2, with the proviso that when n is 0, p and q each represents 1 and when n is 1, p and q are not simultaneously 2.

Figure 1:
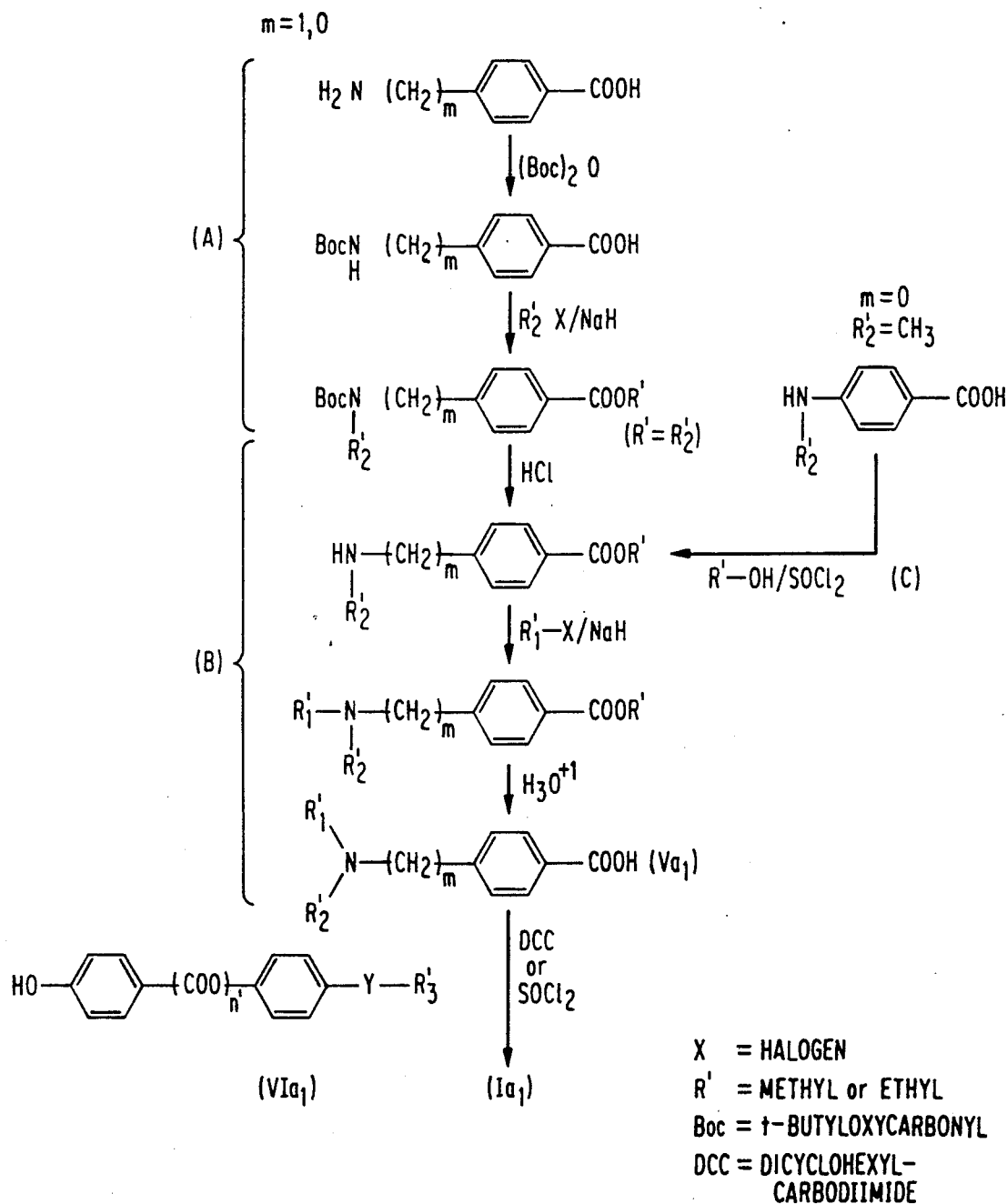
FIG. 1 shows the synthesis scheme of a compound represented by formula (Ia$_1$) described hereinafter.

DETAILED DESCRIPTION OF THE INVENTION $R_1$ in formula (I) described above is a straight chain or branched alkyl group having from 1 to 18 carbon atoms, and preferably from 1 to 16 carbon atoms. The alkyl group may have an asymmetric carbon atom or a part of the alkyl group may be substituted with a halogen atom.

Specific examples of asymmetric alkyl groups shown by $R_1$ are 2-octyl, 2-chloropropyl, and (S)-2-methylbutyl, and (S)-2-methylbutyl is preferred due to low cost.

$R_2$ represents a hydrogen atom or a methyl group and $R_3$ represents a straight chain or branched alkyl group having from 1 to 18 carbon atoms. The alkyl group may also have an asymmetric carbon atom as the alkyl group shown by $R_1$.

$X_1$ and $X_2$ each represents

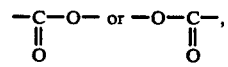

Y represents

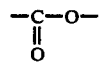

or —O—, and the combination of X's and Y can be desirably selected.

When Y is an ester bond, the amine derivative shown by formula (I) has a greater tendency to exhibit liquid crystal properties as the directions of the ester bonds in the molecule are arranged in one direction, and when Y is —O—, the amine derivative tends to show a liquid crystal property and, in particular, has an easy tendency to exhibit ferroelectric properties.

Of the amine derivatives of this invention, preferred are those represented by formulae (II), (III) and (IV):

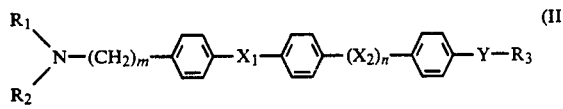
(II)

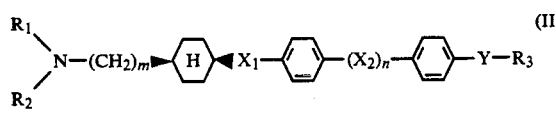
(III)

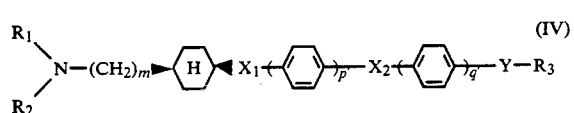
(IV)

wherein $X_1$, $X_2$, Y, $R_1$, $R_2$, $R_3$, m and n are the same as those in formula (I), and p' and q' each represents 1 or 2, provided that p' and q' are not the same.

Particularly preferred compounds in the amine derivatives shown by formula (I) are compounds represented by following formula (Ia), (Ib), or (Ic);

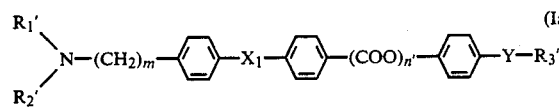
(Ia)

wherein $R_1'$ represents an alkyl group having from 1 to 12 carbon atoms, and preferably from 3 to 8 carbon atoms; $R_2'$ represents a methyl group; $R_3'$ represents a straight chain alkyl group having from 1 to 18 carbon atoms, and preferably from 7 to 18 carbon atoms; $X_1$, Y, and m are the same as those in formula (I); and n' is 0 or 1, and preferably 0;

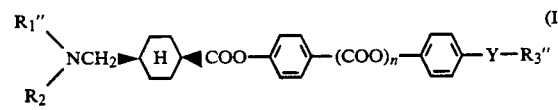
(Ib)

wherein $R_1''$ and $R_3''$ each represents an alkyl group having from 1 to 16 carbon atoms and $R_2$, Y and n are the same as those in formula (I);

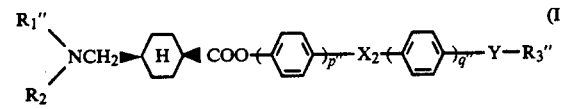
(Ic)

wherein $R_1''$ and $R_3''$ each represents an alkyl group having from 1 to 16 carbon atoms; p'' and q'' each represents 1 or 2, provided that p'' and q'' are not the same; and Y are the same as those in formula (I).

The amine derivative of this invention shown by formula (I) described above comprises an N-substituted amine moiety adjacent to an aromatic ring or a trans-1,4-di-substituted cyclohexane ring, i.e.

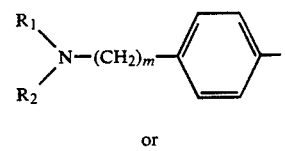

or

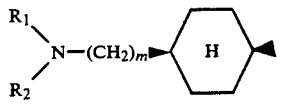

and a biphenyl moiety or a phenylbenzoate moiety, i.e.,

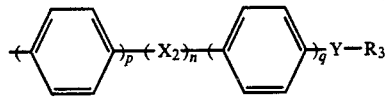

and the two moieties are bonded to each other by an ester bond shown by $X_1$.

The amine derivative of formula (I) can be produced by the esterification reaction of a compound of formula (V) with a compound of formula (VI):

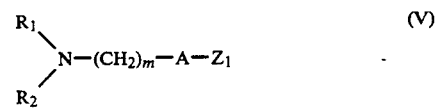
(V)

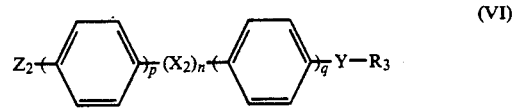
(VI)

wherein A, $X_2$, Y, $R_1$, $R_2$, $R_3$, m, n, p and q are the same as those in formula (I), and $Z_1$ and $Z_2$ represent —COOH and —OH, respectively, or vice versa.

The amine derivatives shown by formula (Ia) are described in detail below.

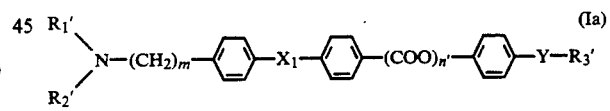
(Ia)

When $X_1$ in formula (Ia) is —COO—, there is a tendency for the cholesteric property of the amine derivative to be increased and when $X_1$ is —OCO—, there is a tendency for the smectic property of the amine derivative to be increased.

Also, when m is 1, the amine derivative has a stronger tendency to exhibit an enantiotropic property than when m is 0 (see, Examples 1 to 9, and Examples 10 and 11 shown hereinbelow). Furthermore, when Y is —COO—, there is a tendency for the melting point of the amine derivative to be lowered as compared with the case when Y is —O—. Hence, the case when Y is —COO— is preferred for practical use (see Examples 1 to 11 shown hereinbelow).

The amine derivatives shown by formula (Ia) can be produced using the following production processes.

First, the production process differs depending on whether the ester bond shown by $X_1$ in formula (Ia) is —COO— or —OCO—.

The compound of formula (Ia) wherein $X_1$ is —COO— [shown by formula ($Ia_1$) below] is obtained by reacting a tertiary amine derivative having a carboxy group at the para-position of the phenyl group thereof [shown by formula ($Va_1$) below] with a phenyl or biphenyl derivative having a hydroxy group at the 4-position of the phenyl or biphenyl derivative [shown by formula ($VIa_1$)].

Also, the compound of formula (Ia) wherein $X_1$ is —OCO— [shown by formula ($Ia_2$) below] is obtained by reacting the same derivatives, except that the above-described carboxy group and hydroxy group are exchanged with each other [shown by formulae ($Va_2$) and ($VIa_2$) below, respectively].

That is, in the case of the amine derivative of formula (Ia) wherein $X_1$ is —COO—, the compound represented by formula ($Ia_1$)

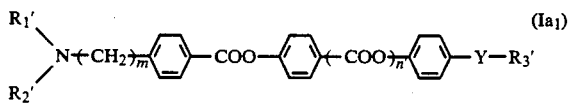
($Ia_1$)

is obtained by esterifying the compound represented by formula ($Va_1$) or a salt thereof

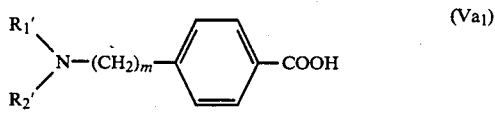
($Va_1$)

and the compound represented by formula ($VIa_1$)

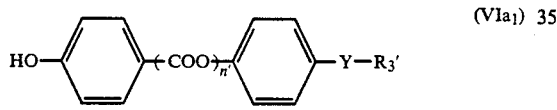
($VIa_1$)

Also, in the case of the compound of formula (Ia) wherein $X_1$ is —OCO—, the compound represented by formula ($Ia_2$)

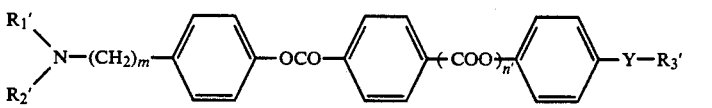
($Ia_2$)

is obtained by esterifying the compound represented by formula ($Va_2$) or a salt thereof

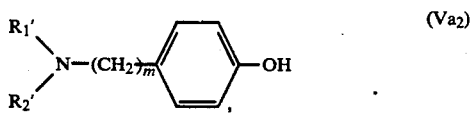
($Va_2$)

and the compound represented by formula ($VIa_2$)

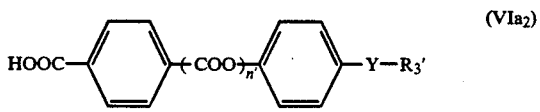
($VIa_2$)

The esterification is carried out using dicyclohexylcarbodiimide (hereinafter, referred to as DCC) or thionyl chloride.

The amine intermediate shown by formula ($Va_1$) or ($Va_2$) is obtained by protecting the active hydrogen atom of each corresponding primary amine with a protecting group and, thereafter, N-alkylating with an alkyl halide having alkyl groups corresponding to $R_1'$ and $R_2'$ using a base such as sodium hydride.

More specifically, the compound shown by formula ($Va_1$) can be obtained as follows. A t-butyloxycarbonyl group, etc., is employed as an amine protecting group for a corresponding commercially available primary amine as a starting material and the amine is N-alkylated with an alkyl halide having an alkyl group corresponding to $R_2'$ (i.e., a methyl halide) and at the same time, esterified, thereby a protecting group for the carboxy group can be formed (see, FIG. 1 (A)). Then, the amine protecting group is removed with an acid such as hydrochloric acid, the amine is N-alkylated with an alkyl halide having an alkyl group corresponding to $R_1'$, and finally, the ester is hydrolyzed to provide the compound of formula ($Va_1$) (see, FIG. 1 (B)).

In particular, when m is 0 and $R_2'$ is a methyl group, the first reaction step (A) in FIG. 1 can be omitted by esterifying commercially available N-methylaminobenzoic acid with methanol or ethanol (see, FIG. 1 (C)).

Figure 2:
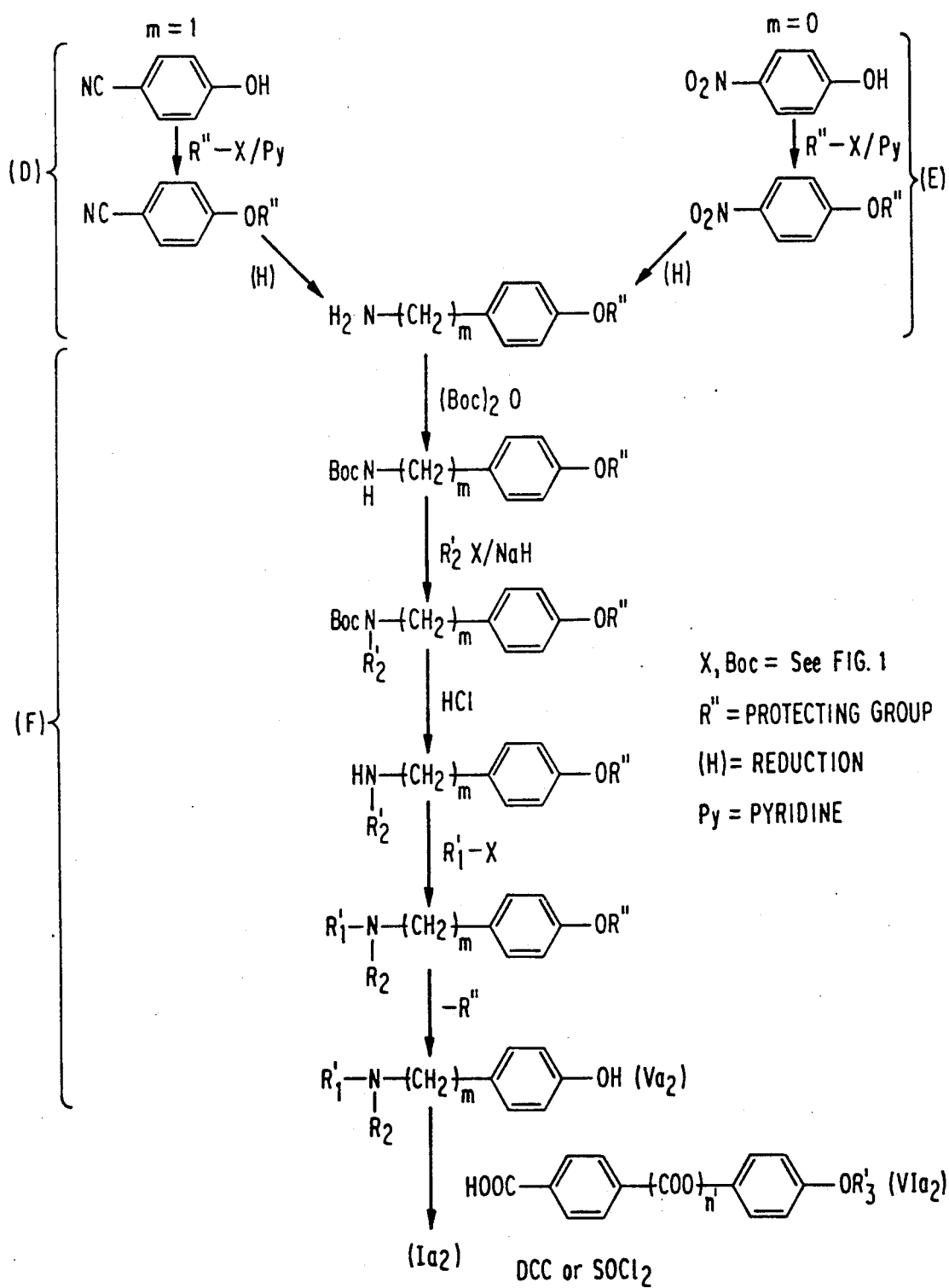
FIG. 2 shows the synthesis scheme of a compound represented by formula (Ia$_2$) described hereinafter.

The compound shown by formula ($Va_2$) can be obtained by reducing a nitrile group when m is 1 or reducing a nitro group when m is 0 to convert it to an amine site (see, FIG. 2 (D) or (E)). After adding a protecting group to each of the phenolic hydroxy group and the amine site, the product is N-alkylated with alkyl halides each having an alkyl group corresponding to $R_1'$ or $R_2'$ (see, FIG. 2 (F)). In this case, a protecting group for the phenolic hydroxy group is necessary, and the above-described reduction reaction and the protecting group-removing reaction can be efficiently carried out using a p-toluenesulfonyl group when m is 1 or a benzyl group when m is 0 as the protecting group.

FIG. 1 shows the reaction scheme for obtaining the compound shown by formula ($Ia_1$) via the amine intermediate shown by formula ($Va_1$). FIG. 2 shows the reaction scheme of obtaining the compound of formula ($Ia_2$) via the amine intermediate shown by formula ($Va_2$).

Each of the compounds produced by the above-described processes is purified by column chromatography or recrystallization.

Figure 4:
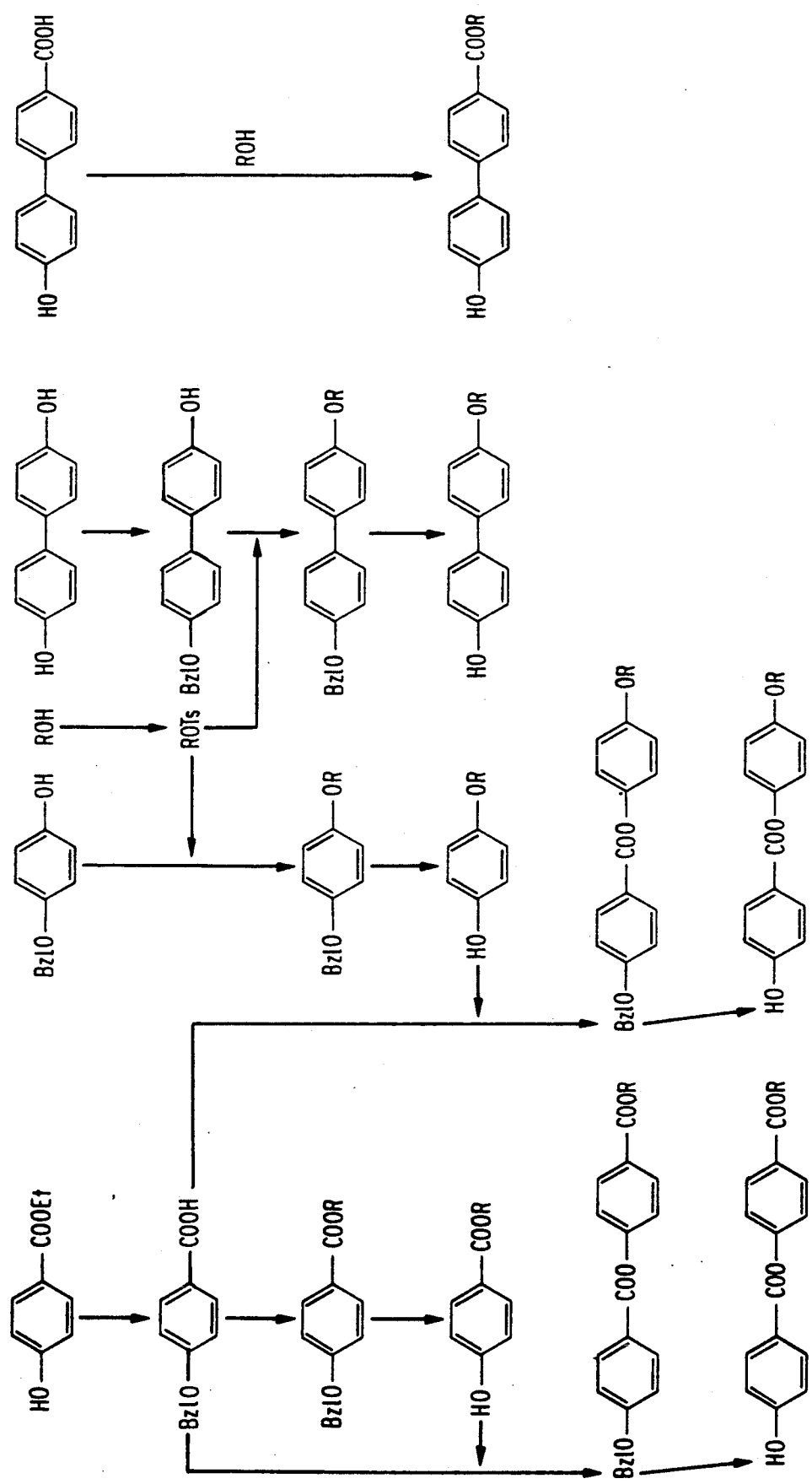
FIG. 4 shows the synthesis scheme of a phenol derivative represented by formula (VIa$_1$) or (VIb$_1$) described hereinafter, which is reacted with the N-alkyltranexamic acid shown by formula (Vb$_1$).

The compound shown by formula ($VIa_1$) can be obtained by the process shown in FIG. 4. Also, commercially available compounds can be used as the compound shown by formula ($VIa_2$).

The compound of this invention shown by formula (Ia) is an amine derivative having a low melting point and showing a very stable liquid crystal property.

The compound of formula (Ia) having an amino group adjacent to a methylene group (i.e., the compound of formula (Ia) wherein m is 1) exhibits enantiotropic liquid crystal properties and this is assumed to be caused due to an acceleration by the amino group of the polarization of the molecule to facilitate a liquid crystal structure formula.

Also, in the compound having an amino group in the form of an aromatic amine (the compound of formula (Ia) wherein m is 0), the liquid crystal properties largely differ depending on the nature of $X_1$ in formula (Ia) (see, Examples 10 and 11 below). This is considered to arise because the conjugated system via the benzene ring is largely in the polarization state and the liquid crystal configuration state of the molecule.

From the above-described facts, it can be seen that the compound having an amine in the molecule improves the liquid crystal property in a manner different from an amide bond having an intermolecular hydrogen bond.

Furthermore, the introduction of an asymmetric carbon atom in the vicinity of the nitrogen atom provides a stable ferroelectric properties over a wide temperature range.

The compound of this invention shown by formula (Ia) is a novel amine derivative useful as a liquid crystal display element with excellent response and memory capability for the above-described reasons.

The amine derivative (tranexamic acid derivative) shown by formula (Ib) is described in detail below.

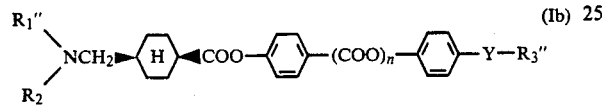
(Ib)

By carrying out alkylation of the amine site and esterification of the C terminal of tranexamic acid, the compound of formula (Ib) showing a stable liquid crystal property over a wide temperature range can be synthesized.

More specifically, at the alkylation of the amino group, the liquid crystal property is changed depending on the nature of the alkyl substitution of the amino group.

$R_1''$ in formula (Ib) is preferably a straight chain or branched alkyl group having from 1 to 16 carbon atoms, and particularly from 5 to 10 carbon atoms from the standpoint of heat stability of the tranexamic acid derivative.

$R_2$ is a hydrogen atom or a methyl group. When $R_2$ is a hydrogen atom, the liquid crystal temperature range of the amine derivative is wide and a smectic phase appears. When $R_2$ is a methyl group, a smectic phase appears but the liquid crystal temperature is narrow.

More specifically, when $R_2$ is a hydrogen atom, the smectic A phase ($S_A$) is very stable, the amine derivative shows $S_A$ regardless of the number of carbon atoms of $R_1''$ and shows $S_A$ in a wide temperature range of 35° C. to 138° C. but if the number of carbon atom of $R_1''$ is too large, the liquid crystal property is reduced.

On the other hand, when $R_2$ is a methyl group, the amine derivative tends to show an unidentified smectic phase ($S_X$) when $R_1''$ is a methyl group, and, as the chain length of $R_1''$ becomes longer, the $S_A$ phase tends to become an $S_C$ phase.

In particular, when $R_1''$ is a branched alkyl group having an asymmetric carbon atom, the amine derivative tends to show the $S_C^*$ phase and to show ferroelectric properties.

The number of carbon atoms of the alkyl group of $R_3''$ is from 1 to 16, and preferably from 5 to 12, but as the number of carbon atoms thereof becomes smaller than 5 or larger than 8, the liquid crystal property of the amine derivative tends to decrease. In addition, the alkyl group may be straight chain or branched, or may have or may not have an asymmetric carbon atom.

Furthermore, when Y of formula (Ib) is —O—, the cholesteric property is increased but as the number of carbon atoms of $R_3''$ increases, the cholesteric property tends to decrease. Also, when Y is —COO—, the smectic property increases.

The tranexamic acid derivative shown by formula (Ib) can be produced by a process similar to the process for the amine derivative of formula (Ia), i.e., by synthesizing an intermediate shown by formula ($Vb_1$)

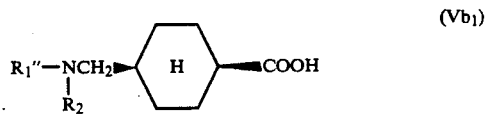
($Vb_1$)

by the N-alkylation of tranexamic acid, and carrying out a dehydration-condensation of the intermediate with a phenol derivative shown by formula ($VIb_1$):

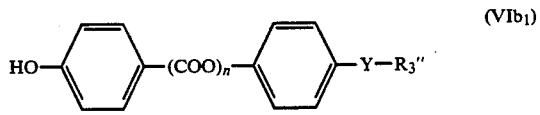
($VIb_1$)

The synthesis process of the N-alkyltranexamic acid shown by formula ($Vb_1$) differs depending on the nature of $R_1''$ and $R_2$.

Figure 3:
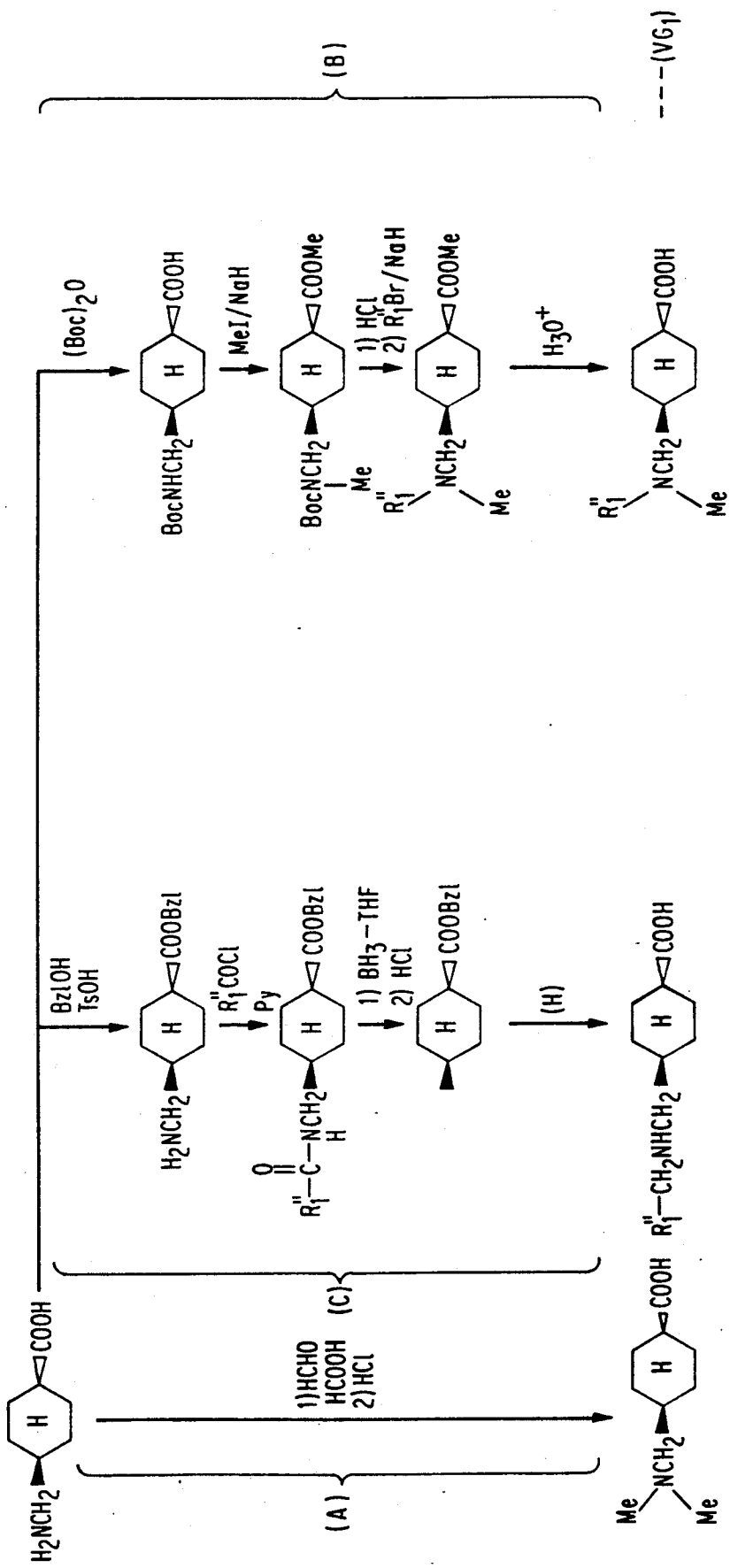
FIG. 3 shows the synthesis scheme of an N-alkyltranexamic acid represented by formula (Vb$_1$) described hereinafter, which is used for the synthesis of a compound represented by formula (Ib) described hereinafter.

More specifically, the compound of formula ($Vb_1$) wherein $R_1''$ and $R_2$ both are a methyl group can be easily obtained simply by refluxing tranexamic acid in water with formaldehyde and formic acid (see FIG. 3 (A)).

The compound of formula ($Vb_1$) wherein $R_1''$ is an alkyl group having from 2 to 16 carbon atoms and $R_2$ is a methyl group can be obtained by protecting the amino group of tranexamic acid with a t-butyloxycarbonyl group, etc., N-methylating the acid using methyl iodide and sodium hydride, and after further removing the t-butyloxycarbonyl group as the protecting group, alkylating the acid using an alkyl bromide having an alkyl group with a number of carbon atoms corresponding to that of $R_1''$ and sodium hydride (see FIG. 3 (B)).

Also, the compound of formula ($Vb_1$) wherein $R_2$ is a hydrogen atom is obtained by reacting a tranexamic acid benzyl ester with an acid chloride having a number of carbon atoms including the carbon atoms of the carboxy group corresponding to that of $R_1''$ under basic conditions to provide an amide, and after selectively reducing the carbonyl group of the amide using borane, de-protecting the benzyl group by hydrogenolysis (see FIG. 3 (C)).

The reaction schematic of the above-described reaction is shown in FIG. 3.

The compound shown by formula ($VIb_1$) described above is obtained by condensing 4-hydroxybenzoic acid or 4-(4'-hydroxyphenyl)benzoic acid with a corresponding alcohol or phenol derivative using thionyl chloride, or obtained by alkylating 4-hydroxyphenol or 4-(4'-hydroxyphenyl)-phenol by reacting it with a corresponding alkyl bromide or alkyl tosylate in the presence of a base. Also, during the synthesis, a protecting group such as benzyl ether, etc., for the hydroxy group must be employed.

The above-described reactions are shown in FIG. 4.

By reacting the compound shown by formula (Vb₁) with the compound shown by formula (VIb₁), the tranexamic acid derivative shown by formula (Ib) can be obtained.

Generally, the condensation reaction of the compound of formula (Vb₁) and the compound of formula (VIb₁) is carried out in an appropriate solvent such as dichloromethane, carbon tetrachloride, benzene, etc., using N,N′-dicyclohexylcarbodiimide (DCC) as a condensing agent, or the compound of formula (Vb₁) is converted into an acid halide thereof using thionyl chloride, etc., and the acid halide is reacted with the compound of formula (VIb₁) under basic conditions.

The compound produced by the above-described process is purified by column chromatography and recrystallization.

An N-alkyltranexamic acid represented by following formula (Vb₁′)

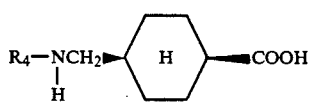

wherein R₄ represents an alkyl group having from 3 to 16 carbon atoms, is an intermediate for the tranexamic acid derivative shown by formula (Ib) and is a novel compound.

The compound of formula (Vb₁′) is produced in the same manner as the above-described process for producing compound shown by formula (Vb₁) wherein R₂ is a hydrogen atom.

An N-methyl-N-alkyltranexamic acid represented by following formula (Vb₁″)

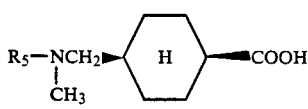

wherein R₅ represents an alkyl group having from 2 to 16 carbon atoms, is an intermediate for the compound of (Ib) (as the compound of formula (Vb₁′)) and is also a novel compound.

The compound of formula (Vb₁″) is produced in the same manner as the above-described process for producing the compound shown by formula (Vb₁) wherein R₁″ is an alkyl group having from 2 to 16 carbon atoms and R₂ is a methyl group.

The compound shown by formula (Ib) described above is a tranexamic acid derivative having a low melting point and showing a very stable liquid crystal property.

The reason that the above-described compound has a stable liquid crystal property over a wide temperature range near room temperature is assumed to be due to not only the low-melting point effect as a result of introduction of the cyclohexane ring but also the amino group which accelerates the polarization of the molecule and assumption of a liquid crystal configuration.

In particular, in the secondary amine compounds, some compounds show the phase configuration of smectic A only in the temperature range above 100° C. (see, Table 3, Examples 14 and 17). The reasons for this are considered to be as follows. It has been considered that an intermolecular hydrogen bond generally reduces the liquid crystal property of compounds having an amide bond, but the hydrogen bond of the amino group is considered to contribute to the stabilization of the liquid crystal molecular configuration.

Also, R₁″ in formula (Ib) is a hydrocarbon residue having an asymmetric carbon atom, ferroelectric properties are achieved (see Table 3 and Examples 23 to 26). This is considered to be because the bond angle of the optically active group is changed due to the influence of the amino group present near the optically active group and the compound has a stereostructure useful to achieve ferroelectric characteristics and is stabilized.

The compound shown by formula (Ib) has excellent durability and thermal stability as described above. It can be used alone as a liquid crystal element for thermal writing, as a liquid crystal element with excellent response and memory capability. Furthermore, the compound of formula (Ib) can be mixed with other liquid crystal compounds to enlarge the temperature range exhibiting liquid crystal properties and can be mixed with conventionally known ferroelectric liquid crystals to improve the response and enlarge the temperature range.

The tranexamic acid derivative shown by formula (Ic) is described in detail below.

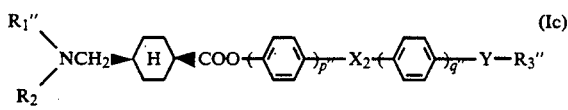

The tranexamic acid derivative as shown above can be synthesized by dehydration-condensing the N-alkylation product of tranexamic acid shown by formula (Vb₁) described above and a phenol derivative represented by following formula (VIc₁);

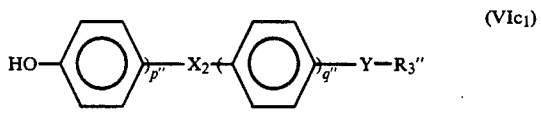

Figure 5:
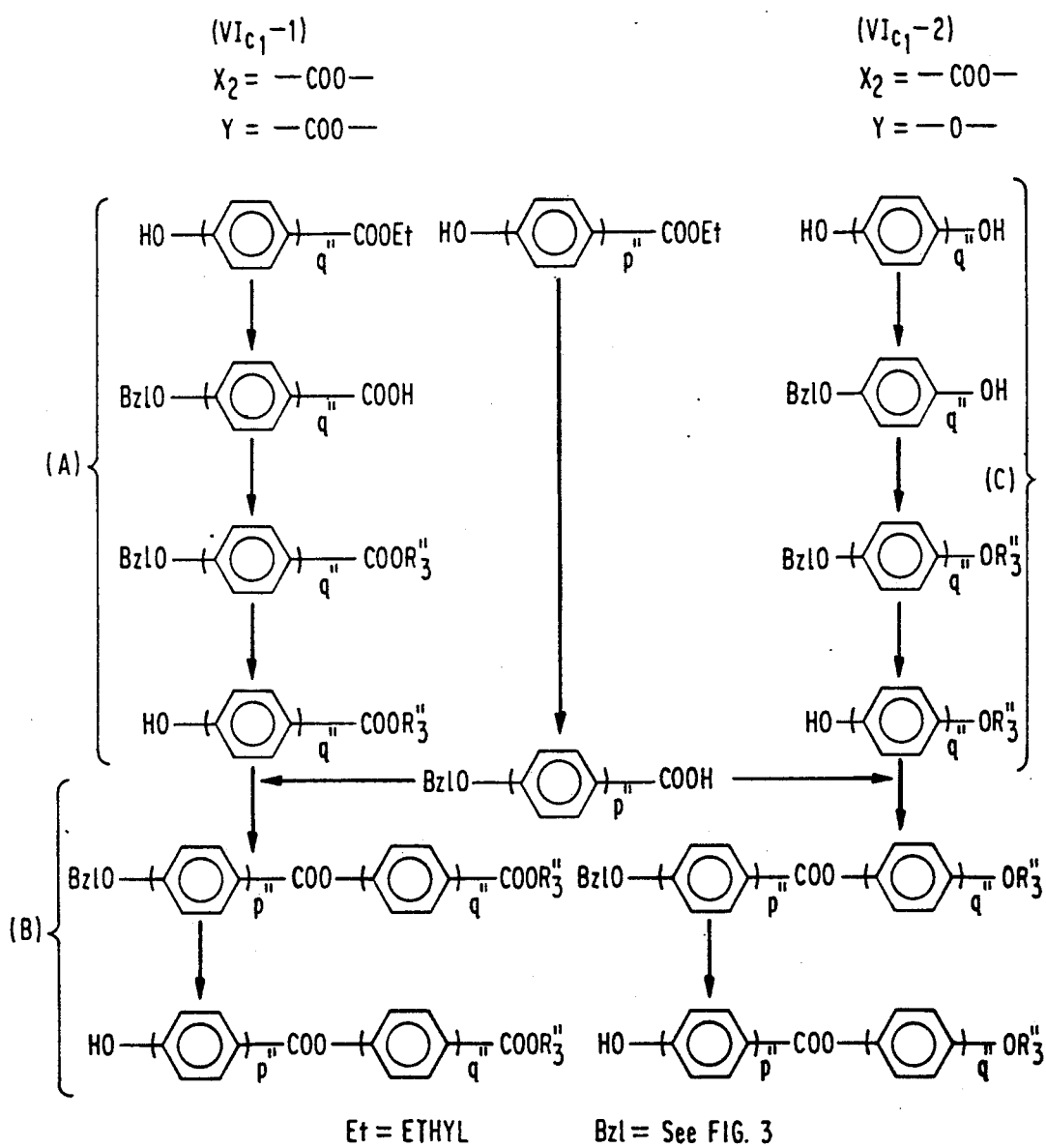
FIG. 5 and FIG. 6 each represents the synthesis scheme of a phenol derivative represented by formula (VIc$_1$) described hereinafter, which is used for the synthesis of a compound represented by formula (Ic) described hereinafter.
Figure 6:
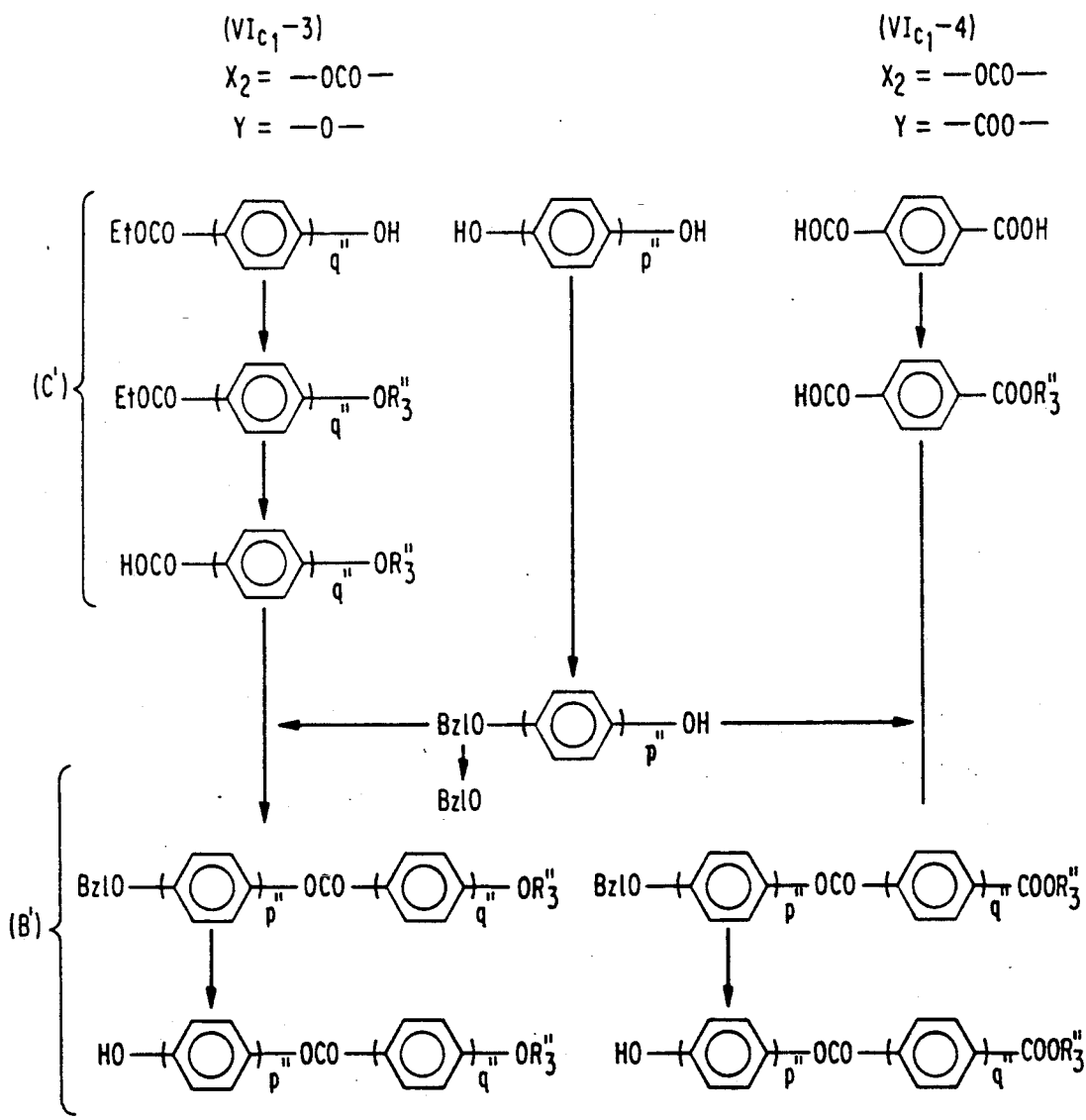

The reaction scheme for producing the compound shown by formula (VIc₁) is set forth in FIG. 5 and FIG. 6.

The compound shown by (VIc₁), which is used as a starting material for producing the compound shown by formula (Ic), comprises 4 kinds of compounds shown by formulae (VIc₁-1) to (VIc₁-4), respectively, shown in FIG. 5 and FIG. 6 depending on the combination of X₂ and Y in formula (VIc₁).

First, for synthesizing the compound shown by formula (VIc₁-1), i.e., the compound of formula (VIc₁) wherein X₂ is —COO— and Y is —COO—, commercially available ethyl 4-hydroxybenzoate or 4-(4′-hydroxyphenyl)benzoic acid is used as the starting material. After protecting the hydroxy group thereof with benzyl ether, etc., the above-described compound is esterified with an alcohol having an alkyl group corresponding to the alkyl group shown by R₃″ in formula (VIc₁) and then deprotected (see, FIG. 5 (A)).

Then, the benzoic acid derivative having the protected hydroxy group obtained in the above-described step is esterified with thionyl chloride, etc., and deprotected to provide the desired compound of formula (VIc₁-1) (see, FIG. 5 (B)).

To synthesize the compound shown by formula (VIc₁-2), i.e., the compound of formula (VIc₁) wherein $X_2$ is —COO— and Y is —O—, a commercially available phenol derivative where one of the hydroxy groups has been protected is etherified with a corresponding alkyl tosylate or alkyl bromide and thereafter is deprotected (see, FIG. 5 (C)).

Thereafter, by following the same procedure as described for producing the compound of (VIc$_1$-1) described above, the desired compound shown by formula (VIc$_1$-2) is obtained.

The compound of formula (VIc$_1$-3), i.e., the compound of formula (VIc$_1$) wherein $X_2$ is —OCO— and Y is —O— can be obtained by etherifying or esterifying commercially available ethyl 4-hydroxybenzoate or 4-(4'-hydroxyphenyl)benzoic acid as in the case of FIG. 5 (C) and by carrying out the reaction as in FIG. 5 (B).

Also, the compound of formula (VIc$_1$-4), i.e., the compound of formula (VIc$_1$) wherein $X_2$ is —OCO— and Y is —COO— can be obtained by esterifying a commercially available dicarboxylic acid with a corresponding alcohol and thereafter carrying out the reaction as in the case of FIG. 5 (B) (see, FIG. 6).

Finally, by reacting the compound of formula (Vb$_1$) and the compound of formula (VIc$_1$) obtained as described above, the tranexamic acid derivative shown by formula (Ic) can be obtained.

Practically, the condensation reaction of the compound of formula (Vb$_1$) and the compound of formula (VIc$_1$) is carried out in an appropriate solvent such as dichloromethane, carbon tetrachloride, benzene, etc., using DCC as a condensing agent. Alternatively, in other process, the compound of formula (Vb$_1$) is converted to an acid halide using thionyl chloride, etc., and the acid halide is reacted with the compound of formula (VIc$_1$) under basic conditions.

The compounds produced by the above-described processes are purified by column chromatography and recrystallization.

The compound of this invention shown by formula (Ic) is a tranexamic acid derivative showing very stable liquid crystal properties.

The reason that the compound has a stable liquid crystal phase over a wide temperature range near room temperature is assumed to be based on that the cyclohexane ring present between the amine and the carboxylic acid and this keeps the core of the molecule as a benzene ring rigid and reduces the melting point as a chemical effect.

On the other hand, depending on the kind of $R_3''$, there is a difference in smectic property. This is assumed to be due to the bending of the molecule caused by the benzene ring and the kind thereof and the bond angle from the long axis of the molecule, that is, the change of the twisted structure of the molecule influences the intermolecular co-reaction and the regularity of the molecular configuration.

The compound shown by formula (Ic) is a novel amino acid derivative useful as a liquid crystal display element with excellent response and memory capability for the above-described reasons. Also, the compound can be mixed with conventionally known ferroelectric liquid crystals to enlarge the temperature range exhibiting ferroelectric characteristics and to improve the response, or can be mixed with an optically inactive liquid crystal to impart ferroelectric characteristics thereto.

The following examples are intended to illustrates the invention more specifically but, are not to be construed to limit the present invention in any way.

In the examples, Cry, Ch, $S_A$, $S_C*$, and Iso phases indicate crystal, cholesteric phase, smectic A phase, chiralsmectic C phase, and isotropic liquid, respectively. Also, $S_X$ shows an unidentified smectic phase structure and r.t. shows room temperature.

The compounds of this invention were purified by silica gel column chromatography and recrystallization with alcohol, hexane, etc.

Also, the measurement of the phase transition point shown below is sometimes influenced to some extent by the purity of the material. Unless otherwise indicated herein, all parts, percents ratios and the like are by weight.

EXAMPLE 1

Synthesis of 4-[N-(S)-2-Methylbutyl-N-methylaminomethyl]-benzoic Acid 4''-Heptyloxycarbonyl-4'-biphenyl Ester (1-1): Synthesis of 4-(N-t-Butyloxycarbonylaminomethyl)benzoic Acid:

In 150 ml of a mixture of dioxane and water (2:1 by volume) was dissolved 7.6 g of 4-aminomethylbenzoic acid, and 50 ml of an aqueous 1 mol sodium hydroxide solution and 25 ml of a dioxane solution of 12.0 g of di-t-butyl dicarbonate were added dropwise to the solution over a period of 10 minutes. Then, after stirring the mixture for 2.5 hours at room temperature (about 20° to 30° C.), the reaction mixture was concentrated under reduced pressure to about ⅓ of the original volume on a water bath of external temperature of from 50° C. to 60° C. and about 40 ml of 1N hydrochloric acid was added dropwise to the reaction mixture under ice-cooling to adjust the pH thereof to from 3 to 4.

Then, the reaction product was extracted three times, each time with 40 ml of ethyl acetate, the organic layer thus obtained was washed with 30 ml of purified water and 30 ml of a saturated aqueous sodium chloride solution, and after drying it with magnesium sulfate, the solvent was distilled off under reduced pressure.

The crude crystals thus obtained were washed with isopropyl ether and then recrystallized from ethyl acetate to provide 9.9 g (yield 79%) of a colorless powder of 4-(N-t-butyloxycarbonylaminomethyl)benzoic acid.

(1-2): Synthesis of 4-(N-t-Butyloxycarbonyl-N-methylaminomethyl)benzoic Acid Methyl Ester:

In 80 ml of dimethylformamide (DMF) were dissolved 8.8 g of the compound obtained in step (1-1) above and 17.4 ml of methyl iodide and then 4.2 g of 60% sodium hydride (a dispersion of 60% sodium hydride in mineral oil) was added little by little to the solution with stirring slowly under ice-cooling.

Then, after stirring the mixture overnight at room temperature, the mixture was diluted with 80 ml of ethyl ether and 5 ml of purified water was added dropwise thereto under ice-cooling. The organic layer formed was collected and after successively washing such three times, each time with 20 ml of purified water, once with 20 ml of a saturated aqueous sodium hydrogen carbonate solution, and then with 20 ml of a saturated aqueous sodium chloride solution, the organic layer was dried with magnesium sulfate. Then, by distilling off the solvent under reduced pressure, 12.2 g (yield 100%) of a yellow oily crude 4-(N-t-butyloxycarbonyl-N-methylaminomethyl)benzoic acid methyl ester was obtained.

(1-3): Synthesis of 4-(N-(S)-2-Methylbutyl-N-methylaminomethyl)benzoic Acid Methyl Ester:

To 12.2 g of the compound obtained in step (1-2) above was added 20 ml of an ethyl acetate solution of 4N hydrochloric acid under ice-cooling and after stirring the mixture for one hour, the crystals formed were collected by filtration to provide 6.8 g (yield 90%) of 4-(N-methylaminomethyl)benzoic acid methyl ester hydrochloride. Then, 6.5 g of the crystals thus obtained was dissolved in 30 ml of DMF and 4.2 ml of triethylamine and 5.0 g of (S)-2-methylbutyl bromide were added to the solution under ice-cooling. Then, 1.3 g of 60% sodium hydride was added little by little to the solution and the mixture was heated to 80° C. for from 1 to 2 hours. After cooling, the reaction mixture was diluted with 80 ml of diethyl ether and 5 ml of purified water was added dropwise slowly to the solution. The organic layer formed was collected and, after successively being washed with 20 ml of purified water, 20 ml of a saturated aqueous sodium hydrogen carbonate solution, and then 20 ml of a saturated aqueous sodium chloride solution, dried with magnesium sulfate, and then the solvent was distilled off under reduced pressure.

The yellow oily product thus obtained was subjected to column chromatography using 80 g of silica gel and from a fraction of ethyl acetate-hexane (1:6 by volume), 3.9 g (yield 52%) of colorless oily 4-(N-(S)-2-methylbutyl-N-methylaminomethyl)benzoic acid methyl ester was obtained.

(1-4): Synthesis of 4-(N-(S)-2-Methylbutyl-N-methylaminomethyl)benzoic Acid Hydrochloride:

In 10 ml of 6N hydrochloric acid was dissolved 3.9 g of the compound obtained in step (1-3) above and the solution was stirred for 6 hours at 50° C. Then, the solvent was distilled off under reduced pressure and the residue formed was recrystallized from a mixture of isopropanol and diethyl ether (about 3:1 by volume) to provide 3.4 g (yield 80%) of colorless powdery 4-(N-(S)-2-methylbutyl-N-methylaminomethyl)benzoic acid hydrochloride.

(1-5): Synthesis of the Title Compound:

In 3 ml of dichloromethane were dissolved 147 mg of the compound obtained in step (1-4) above and 185 mg of 4-hydroxy-4'-biphenylcarboxylic acid heptyl ester obtained in a similar manner to that in step (12-2) described below and after adding thereto 134 mg of dicyclohexylcarbodiimide and 8 mg of 4-pyrrolidinopyridine, the mixture was stirred overnight at room temperature. Then the solvent was distilled off under reduced pressure and after adding 20 ml of ethyl acetate to the residue followed by stirring for a while and filtering. The crystals obtained were dissolved in 30 ml of a saturated aqueous sodium hydrogen carbonate solution and after removing insoluble matter, the product was extracted three times, each time with 20 ml of ethyl acetate. The organic layer thus obtained was washed with 20 ml of a saturated aqueous sodium chloride solution and after drying with magnesium sulfate, the solvent was distilled off under reduced pressure.

Recrystallization of the crude crystals was carried out twice from hexane to obtain 43 mg (yield 15%) of the colorless powdery title compound shown by formula (Ia) wherein $X_1$ is —COO—, m is 1 and $R_1'$, $R_2'$, $R_3'$, Y and n' are shown in Table 1 below.

The structure of the compound obtained was confirmed by $^1$H-NMR and IR.

The results obtained by measuring the phase transition temperature of the compound obtained is shown in Table 1 below. The phase transition temperature was determined by visual observation with a polarization microscope and a differential scanning calorimeter.

Furthermore, the value of the spontaneous polarization thereof is also shown in Table 1. The spontaneous polarization was measured as follows.

Measurement of Spontaneous Polarization

After forming an isotropic liquid by heating the compound, the liquid was placed in a cell of 3.3 μm in thickness composed of a glass plate having a transparent electrode, where this glass plate had been coated with a polyamide and subjected to a rubbing treatment, and the temperature was lowered slowly from the isotropic liquid start to form a smectic phase. Furthermore, the temperature was further lowered from the state and at a temperature of 10° C. lower than the temperature resulting in the Sc* phase, the value of the spontaneous polarization was measured by the triangular wave voltage application method described in Miyasato et al, *Japanese Journal of Applied Physics*, Vol. 22, No. 10, p.L661, 1983 (applied voltage 30 $V_{p-p}$, 50 Hz).

EXAMPLES 2 AND 3

Synthesis of 4-[N-(S)-2-Methylbutyl-N-methylaminomethyl]-benzoic Acid 4''-Alkyloxycarbonyl-4'-biphenyl Ester Compounds of Examples 2 and 3 shown by formula (Ia) described above wherein $X_1$ was —COO—, m was 1, and $R_1'$, $R_2'$, $R_3'$, Y and n', as shown in Table 1 below, were synthesized in the same manner as Example 1.

The structure each of the compounds obtained was confirmed by $^1$H-NMR and IR. Also the phase transition temperature and the spontaneous polarization of each compound were measured by the methods shown in Table 1 and the results are shown in Table 1 below.

EXAMPLES 4 TO 8

Synthesis of 4-(N-(S)-2-Methylbutyl-N-methylaminomethyl)benzoic Acid 4''-Alkoxy-4'-biphenyl Ester Compounds of Examples 4 to 8 shown by formula (Ia) wherein $X_1$ was —COO—, m was 1, and $R_1'$, $R_2'$, $R_3'$, Y and n' as shown in Table 1 below were synthesized as in Example 1.

The structure of each of the compounds obtained was confirmed by $^1$H-NMR and IR.

The phase transition temperatures and the spontaneous polarizations of these compounds were measured by the methods described in Example 1 and the results obtained are shown in Table 1 below.

EXAMPLE 9

Synthesis of 4-Tetradecyloxy-4'-biphenylcarboxylic Acid 4[N-(S)-2-Methylbutyl-N-methylaminomethyl]phenyl Ester (9-1): Synthesis of 4-Aminomethylphenyl Tosylate:

In 60 ml of dichloromethane was dissolved 3.64 g of p-cyanophenol and after adding dropwise 4.2 ml of triethylamine and 10 ml of a dichloromethane solution of 5.72 g of p-toluenesulfonyl chloride to the solution under ice-cooling, the mixture was stirred for 2 hours at room temperature.

The reaction mixture thus obtained was successively washed twice each time with 10 ml of purified water and then once with 10 ml of a saturated aqueous sodium chloride solution, dried with magnesium sulfate, and then the solvent was distilled off under reduced pressure to produce 8.0 g of crude crystals of 4-cyanophenyl tosylate.

In 200 ml of tetrahydrofuran (THF) was suspended 2.28 g of lithium aluminum hydride and after adding dropwise 20 ml of a THF solution of 3.1 g of concentrated (98%) sulfuric acid to the suspension under ice-cooling, the mixture was stirred for one hour at room temperature. Then, 80 ml of a THF solution of 8.0 g of 4-cyanophenyl tosylate was added dropwise to the solution and the mixture was heated to 50° C. for 2 hours. Then, the mixture was ice-cooled again, 30 ml of a mixture of THF and purified water (1:1 by volume) was slowly added thereto followed by stirring until the generation of gas was stopped, and 50 ml of an aqueous solution of 10% sodium hydroxide was further added to the mixture.

The organic layer formed was separated and the aqueous layer was extracted twice each time with 50 ml of diethylether. The organic layer was mixed with the ether extracts and the mixture was washed twice, each time with 30 ml of purified water and once with 30 ml of a saturated aqueous sodium chloride solution, and after drying with magnesium sulfate, the solvent was distilled off under reduced pressure to provide 8.8 g (yield 100%) of the crude crystals of 4-aminomethylphenyl tosylate.

(9-2): Synthesis of 4-[N-(S)-Methylbutyl-N-methylaminomethyl]-phenyl Tosylate:

The compound obtained in step (9-1) above was N-alkylated in the manner described in steps (1-1) to (1-3) in Example 1 to provide colorless oily 4-[N-(S)-2-methylbutyl-N-methylaminomethyl]phenyl tosylate.

(9-3): Synthesis of 4-[N-(S)-2-Methylbutyl-N-methylamino]-phenol Hydrochloride:

In 100 ml of a mixture of ethanol and an aqueous 0.5N sodium hydroxide solution (1:1 by volume) was dissolved 785 mg of the compound obtained in step (9-2) above and the solution was refluxed for 2 hours. The reaction mixture obtained was ice-cooled and after neutralization with acetic acid, the product was extracted three times each time with 50 ml of diethyl ether. The organic layer (extracts) was successively washed with 50 ml of a saturated aqueous sodium hydrogen carbonate and 50 ml of a saturated aqueous sodium chloride solution and, after drying with magnesium sulfate, the solvent was distilled off under reduced pressure. To the residue was added 10 ml of an ethyl acetate solution of 4N hydrochloric acid, and the solvent was distilled off again under reduced pressure to produce 350 mg (yield 66%) of 4-[N-(S)-2-methylbutyl-N-methylamino]-phenol hydrochloride.

(9-4): Synthesis of the Title Compound:

By following the same procedure as in step (1-5) in Example 1 using 350 mg of the compound obtained in step (9-3) above and 687 mg of 4-tetradecyloxy-4'-biphenylcarboxylic acid, 200 mg (yield 24%) of the above-described title compound was obtained.

The structure of the compound obtained was confirmed by ¹H-NMR and IR. Furthermore, the phase transition temperature and the spontaneous polarization of the compound were measured by the methods described in Example 1 and the results obtained are shown in Table 1.

EXAMPLE 10

Synthesis of 4-[N-(S)-2-Methylbutyl-N-methylamino]-benzoic Acid 4-Octyloxy-4'-biphenyl Ester (10-1): Synthesis of 4-[N-(S)-Methylbutyl-N-methylamino]benzoic Acid Hydrochloride:

After cooling 20 ml of methanol to −10° C., 3 ml of thionyl chloride was added dropwise thereto and after stirring the mixture for 10 minutes, 4.0 g of 4-methylaminobenzoic acid obtained from a commercial source was added to the mixture followed by stirring overnight at room temperature. Then, the solvent was distilled off under reduced pressure, 10 ml of diethyl ether was added to the residue to form crystals, which were collected by filtration to obtain 5.0 g (yield 93%) of 4-methylaminobenzoic acid methyl ester hydrochloride. Then, by following the same procedures as in steps (1-3) and (1-4) in Example 1, 4-[N-(S)-2-methylbutyl-N-methylamino]-benzoic acid hydrochloride was obtained via 4-[N-(S)-2-methylbutyl-N-methylamino]benzoic acid methyl ester.

(10-2): Synthesis of the Title Compound:

In 5 ml of carbon tetrachloride was dissolved 221 mg of the compound obtained in step (10-1) above and after adding thereto 0.2 mol of thionyl chloride and one drop of N,N-dimethylformamide, the mixture was refluxed for one hour. The solvent was distilled off under reduced pressure, the residue formed was dissolved in 5 ml of toluene, and after adding dropwise a solution of 358 mg of 4-octyloxy-4'-hydroxybiphenyl, which was obtained by an ordinary method, in a mixture of 5 ml of toluene and 1 ml of pyridine to the solution under ice-cooling, the mixture was refluxed for one hour.

After cooling, the reaction mixture was diluted with 30 ml of ethyl acetate, the solution was successively washed twice each time with 10 ml of purified water, and once with 10 ml of a saturated aqueous sodium chloride solution, and after drying with magnesium sulfate, the solvent was distilled off under reduced pressure.

The residue obtained was column chromatographed using 30 g of silica gel and the fraction of 10% ethyl acetate-hexane was concentrated and recrystallized to obtain 120 mg (yield 24%) of the colorless acicular title compound.

The structure of the compound obtained was confirmed by ¹H-NMR and IR. Furthermore, the phase transition temperature of the compound were measured by the methods described in Example 1 and the results obtained is shown in Table 1.

EXAMPLE 11

Synthesis of 4-Octyloxy-4'-biphenylcarboxylic Acid 4-[N-(S)-2-Methylbutyl-N-methylamino]phenyl Ester (11-1): Synthesis of 4-Benzyloxyaniline Hydrochloride:

In 40 ml of ethanol was dissolved 4.17 g of p-nitrophenol and after adding 2.5 g of potassium carbonate and 3.9 ml of benzyl bromide to the solution, the mixture was refluxed for 1.5 hours.

The reaction mixture thus obtained was cooled and the crystals deposited were collected by filtration and washed with purified water. Then, the crude crystals obtained were recrystallized from ethanol to provide 6.4 g (yield 94%) of colorless acicular p-nitrophenol benzyl ether.

In 20 ml of acetic acid was suspended 2.3 g of p-nitrophenol benzyl ether obtained and, after adding thereto 20 g of a zinc powder, the mixture was stirred overnight at room temperature. Insoluble matter was removed, the reaction mixture was concentrated, and after adding thereto 50 ml of ethyl acetate, was successively washed with 20 ml of an aqueous 10% sodium hydroxide solution and 20 ml of a saturated sodium chloride solution. After drying with magnesium sulfate, the solvent was distilled off. The residue formed was dissolved in 20 ml of an ethyl acetate solution of 4N hydrochloric acid and the solvent was distilled off to obtain 1.5 g (yield 63%) of crude crystals of 4-benzyloxyaniline hydrochloride.

(11-2): Synthesis of 4-[N-(S)-2-Methylbutyl-N-methylamino]phenol Benzyl Ether

By alkylating the compound obtained in step (11-1) above in the manner described in steps (1-1) to (1-3) above, colorless oily 4-[N-(S)-2-methylbutyl-N-methylamino]phenol benzyl ether was obtained.

(11-3): Synthesis of 4-[N-(S)-2-Methylbutyl-N-methylamino]phenol:

In 10 ml of ethanol were dissolved 1.0 g of the compound obtained in step (11-2) above and 100 mg of palladium black and after adding thereto 2 ml of cyclohexane, the mixture was refluxed for one hour. After removing insoluble matter from the reaction mixture, the solvent was distilled off under reduced pressure to obtain 610 mg (yield 86%) of light-yellow oily 4-[N-(S)-2-methylbutyl-N-methylamino]phenol.

(11-4): Synthesis of the Title Compound:

By following the same procedure as in step (10-2) in Example 10 using 652 mg of 4-octyloxy-4'-phenylcarboxylic acid and 290 mg of the compound obtained in step (11-3) above, 580 of (yield 77%) of the title compound was obtained.

The structure of the compound obtained was confirmed by $^1$H-NMR and IR. Furthermore, the phase transition temperature and spontaneous polarization were measured using the methods described in Example 1 and the results are shown in Table 1 below.

In addition, the $^1$H-NMR and IR data of the compounds obtained in Examples 1 to 11 are shown in Table 2 below.

TABLE 1

| Example No. | $R_1'$ | $R_2'$ | $R_3'$ | $X_1$ | Y | m | n' | Phase Transition Temperature[*1] Cry—$S_X^*$—$S_C^*$—$S_A$—Ch—$I_{SO}$ (°C.) | | | | | Spontaneous Polarization (nC/cm$^2$) |
|---|---|---|---|---|---|---|---|---|---|---|---|---|---|
| 1 | CH$_3$CH$_2$CHCH$_2$— \| CH$_3$ | —CH$_3$ | —C$_7$H$_{15}$ | —COO— | —COO— | 1 | 0 | •33 | •44 | •61 | •73 | • | 0.9 |
| 2 | CH$_3$CH$_2$CHCH$_2$— \| CH$_3$ | —CH$_3$ | —C$_5$H$_{11}$ | —COO— | —COO— | 1 | 0 | •33 | •56 | | •78 | • | — |
| 3 | CH$_3$CH$_2$CHCH$_2$— \| CH$_3$ | —CH$_3$ | —C$_{12}$H$_{25}$ | —COO— | —COO— | 1 | 0 | •30 | •51 | •59 | •67 | • | 0.1 |
| 4 | CH$_3$CH$_2$CHCH$_2$— \| CH$_3$ | —CH$_3$ | —C$_8$H$_{17}$ | —COO— | —O— | 1 | 0 | •68 | •103 | •114 | •128 | • | 0.3 |
| 5 | CH$_3$CH$_2$CHCH$_2$— \| CH$_3$ | —CH$_3$ | —C$_{12}$H$_{25}$ | —COO— | —O— | 1 | 0 | •<25 | •93 | •111 | •115 | • | 0.6 |
| 6 | CH$_3$CH$_2$CHCH$_2$— \| CH$_3$ | —CH$_3$ | —C$_{14}$H$_{29}$ | —COO— | —O— | 1 | 0 | •48 | •83 | •105 | •109 | • | 0.1 |
| 7 | CH$_3$CH$_2$CHCH$_2$— \| CH$_3$ | —CH$_3$ | —C$_{16}$H$_{33}$ | —COO— | —O— | 1 | 0 | •65 | •82 | •104 | •107 | • | 2.1 |
| 8 | CH$_3$CH$_2$CHCH$_2$— \| CH$_3$ | —CH$_3$ | —C$_{18}$H$_{37}$ | —COO— | —O— | 1 | 0 | •72 | •75 | •104 | •107 | • | 0.8 |
| 9 | CH$_3$CH$_2$CHCH$_2$— \| CH$_3$ | —CH$_3$ | —C$_{14}$H$_{29}$ | —OCO— | —O— | 1 | 0 | •41 | •70 | •120 | •127 | • | 0.5 |
| 10 | CH$_3$CH$_2$CHCH$_2$— \| CH$_3$ | —CH$_3$ | —C$_8$H$_{17}$ | —COO— | —O— | 0 | 0 | •81 | | | •101 | • | — |

TABLE 1-continued

| Example No. | R$_1$' | R$_2$' | R$_3$' | X$_1$ | Y | m | n' | Phase Transition Temperature*¹ Cry—S$_X$*—S$_C$*—S$_A$—Ch—I$_{SO}$ (°C.) | Spontaneous Polarization (nC/cm²) |
|---|---|---|---|---|---|---|---|---|---|
| 11 | CH$_3$CH$_2$CHCH$_2$—<br>\|<br>CH$_3$ | —CH$_3$ | —C$_8$H$_{17}$ | —OCO— | —O— | 0 | 0 | •<25  •60  •104  •113  • | 2.7 |

(Note)
*¹Temperature at which the compound exhibits the defined phases in the course of decrease in temperature are given. (For example, the compound of Example 1 exhibits a cholesteric phase at 73° C., a chiralsmectic C phase at 61° C., an unidentified smectic phase at 44° C., and a crystal phase at 33° C.) In Tables 3 and 6 described below, the results are shown in the same manner.

TABLE 2

| Example No. | IR Spectrum (cm⁻¹) | NMR Spectrum (ppm) |
|---|---|---|
| 1-3 | 2795, 2775, 1735, 1715, 1610, 1495 | 0.89, 0.91, 1.00–1.71*², 1.74–1.89, 2.11, 2.20, 2.23, 3.51, 3.60, 4.36, 7.34, 7.53, 7.69, 7.70, 8.13, 8.17 |
| 4–8 | 2795, 2775, 1740, 1610, 1495 | 0.89, 0.91, 1.00–1.71*² 1.74–1.89, 2.11, 2.19, 2.23, 3.51, 3.60, 4.00, 6.99, 7.26, 7.50, 7.51, 7.60, 8.16 |
| 9 | 2795, 2760, 1735, 1605, 1500 | 0.89, 0.91, 0.94–1.70, 1.74–1.91, 2.11, 2.17, 2.23, 3.43, 3.51, 4.03 7.00, 7.17, 7.40, 7.60, 7.69, 8.23 |
| 10 | 1725, 1610, 1500, 1285 | 0.91, 0.92, 0.94, 1.06–1.66, 1.69–1.97, 3.09, 3.17, 3.37, 4.00, 6.69, 6.97, 7.23, 7.51, 7.57, 8.06 |
| 11 | 1725, 1605, 1515, 1275 | 0.89, 0.91, 0.93, 1.01–1.71, 1.74–1.89, 2.97, 3.04, 3.23, 4.03, 6.69, 7.00, 7.09, 7.63, 7.69, 8.20 |

(Note)
*²Peak heights varied depending on the chain lengths of alkylene group in the compounds, respectively.

It is clear from the above results that the compounds of this invention shown by formula (Ia) exhibit a ferroelectric characteristics over a very wide temperature range. Accordingly, the invention provides simply and at low cost, novel compounds useful as a material for a liquid crystal display element utilizing an electrooptic effect over a practical temperature range alone or as a mixture with other suitable nematic, smectic, or ferroelectric liquid crystals.

EXAMPLE 12

Synthesis of trans-4-(N,N-Dimethylaminomethyl)cyclohexanecarboxylic Acid 4''-(2-Methylbutyloxycarbonyl)-4'-biphenyl Ester (12-1): Synthesis of trans-4-(N,N-Dimethylaminomethyl)cyclohexanecarboxylic Acid Hydrochloride:

In 5 ml of purified water was dissolved 4.72 g of tranexamic acid and after adding thereto 2.5 ml of an aqueous solution of 35% formaldehyde and 6.4 ml of formic acid, the mixture was refluxed for 9 hours.

After further stirring the mixture for 12 hours at room temperature, 4.5 ml of concentrated hydrochloric acid was added to the mixture and the solvent was distilled off under reduced pressure.

Then, 30 ml of toluene was added to the residue, the solvent was distilled off again under reduced pressure, and after confirming that an irritating odor had vanished, diethyl ether was added thereto to form crystals. The crystals were collected by filtration to obtain 4.76 g (yield 71.6%) of colorless flaky crystals of trans-4-(N,N-dimethylaminomethyl)cyclohexanecarboxylic acid hydrochloride.

The structure of the compound obtained was confirmed by ¹H-NMR and IR.

(12-2): Synthesis of 4-(4'-Hydroxyphenyl)benzoic Acid 2-Methylbutyl Ester:

A mixture of 2.14 g of 4-(4'-hydroxyphenyl)benzoic acid, 5.4 ml of 2-Methyl butanol, and 57 mg of p-toluenesulfonic acid mono-hydrate was stirred for 3 hours at 120° C. After cooling, the mixture was diluted with 50 ml of dichloromethane, successively washed with 20 ml of a saturated aqueous sodium hydrogen carbonate solution and 20 ml of a saturated aqueous sodium chloride solution, and after drying with magnesium sulfate, the solvent was distilled off under reduced pressure.

The crystals obtained were washed several times with cold hexane and recrystallized from hexane to obtain 1.6 g (yield 57%) of colorless acicular 4-(4'-hydroxyphenyl)benzoic acid 2-methylbutyl ester.

(12-3): Synthesis of the Title Compound:

In 5 ml of dichloromethane were dissolved 532 mg of the compound obtained in step (12-1) above and 568 mg of the compound obtained in step (12-2) above and after adding thereto 495 mg of DCC under ice-cooling, the mixture was stirred for 3 hours and further stirred overnight at room temperature.

The solvent was distilled off under reduced pressure from the reaction mixture and, after adding 30 ml of ethyl acetate to the residue followed by stirring for a while, the mixture was filtered. The crystals obtained were dissolved in 30 ml of dichloromethane and insoluble matter was filtered away. The organic layer formed was successively washed with 5 ml of a saturated aqueous sodium hydrogen carbonate solution and 5 ml of a saturated aqueous sodium chloride solution, and after drying with magnesium sulfate, the solvent was distilled off under reduced pressure.

The crude crystals obtained were recrystallized from hexane to obtain 202 mg (yield 22%) of the colorless powdery title compound.

The structure of the compound obtained was confirmed by ¹H-NMR and IR.

EXAMPLE 13

Synthesis of 4-[trans-4'-(N,N-Dimethylaminomethyl)cyclohexylcarbonyloxy]benzoic Acid 4''-(2-Methylbutyloxycarbonyl)phenyl Ester (13-1): Synthesis of 4-Hydroxybenzoic Acid 4'-(2-Methylbutyloxycarbonyl)phenyl Ester:

After refluxing 6.54 g of p-benzyloxybenzoic acid and 12.5 g of thionyl chloride in 40 ml of carbon tetrachloride for 3 hours, unreacted thionyl chloride and residual carbon tetrachloride were distilled off and the residue was dissolved in 10 ml of toluene. Then, after adding dropwise thereto 30 ml of a solution of 1.64 g of 2-methylbutyl alcohol in a mixture of toluene and pyridine (4:1 by volume), the mixture was refluxed for 3 hours. After the reaction was over, 30 ml of ethyl acetate was added to the reaction mixture and the mixture was successively washed with 30 ml of purified water, 30 ml of 5% hydrochloric acid, 30 ml of a saturated aqueous sodium hydrogen carbonate solution, and then 30 ml of a saturated aqueous sodium chloride solution and dried with magnesium sulfate.

After distilling off ethyl acetate from the reaction mixture, the residue was purified by silica gel column chromatography using a mixture of n-hexane and ethyl acetate (10:1 by volume) as an eluent to obtain 4.49 g of a colorless oily product.

Then, the oily product was dissolved in 15 ml of ethanol and the solution was refluxed for one hour in the presence of 6.75 g of cyclohexene and 0.45 g of palladium black. The reaction mixture was filtered to remove palladium black and ethanol and cyclohexene were distilled off to obtain 2.99 g (yield 93%) of 2-methylbutyl 4-hydroxybenzoate.

Then, after refluxing 0.80 g of p-benzyloxybenzoic acid and 4.17 g of thionyl chloride in 15 ml of carbon tetrachloride for 3 hours, excess thionyl chloride and carbon tetrachloride were distilled off, a solution of 0.73 g of the 2-methylbutyl 4-hydroxybenzoate described above dissolved in 7 ml of toluene was added to the residue and after further adding thereto 3.50 g of pyridine, the mixture was stirred for 3 hours at 80° C. After the reaction was over, 30.0 ml of ethyl acetate was added to the reaction mixture and the mixture was successively washed with 10 ml of 5% hydrochloric acid, 10 ml of a saturated aqueous sodium hydrogen carbonate solution, and 10 ml of a saturated aqueous sodium chloride solution, and dried with magnesium sulfate.

Then, ethyl acetate was distilled off from the reaction mixture and the residue was recrystallized from methanol to obtain 0.89 g of 4'-(2-methylbutyloxycarbonyl)phenyl 4-benzyloxybenzoate.

Then, the product was dissolved in 10.0 ml of ethanol and the solution was refluxed for one hour in the presence of 1.01 g of cyclohexene and 0.18 g of palladium black. After filtering the reaction mixture to remove the palladium black, ethanol and cyclohexene were distilled off to obtain 0.69 g (yield 60%) of 4-hydroxybenzoic acid 4'-(2-methylbutyloxycarbonyl)phenyl ester.
(13-2): Synthesis of the Title Compound:

In 3 ml of dichloromethane were dissolved 266 mg of the compound obtained in step (12-1) above in Example 12 and the compound obtained in step (13-1) above, and after adding thereto 240 mg of DCC under ice-cooling, the reaction was carried out the same manner as in step (12-3) above in Example 12, and the reaction product was recrystallized from hexane to obtain 259 mg (yield 52%) of the colorless powder of the above-described title compound.

The structure of the compound obtained was confirmed by $^1$H-NMR and IR.

EXAMPLE 14

Synthesis of trans-4-(N-Heptylaminomethyl) cyclohexanecarboxylic Acid 4''-(2-Methylbutyloxycarbonyl)-4'-biphenyl Ester (14-1): Synthesis of trans-4-Aminomethylcyclohexanecarboxylic Acid Benzyl Ester Tosylate:

In 30 ml of toluene were suspended 4.72 g of tranexamic acid and 15 ml of benzyl alcohol and after adding 6.84 g of p-toluenesulfonic acid to the suspension, the mixture was refluxed for 3 hours while removing water formed using a Dean-Stark trap.

After confirming that the reaction mixture was transparent, the reaction mixture was cooled. The crystals deposited were collected by filtration and recrystallized from ethanol to obtain 11.5 g (yield 99%) of colorless acicular tranexamic acid benzyl ester tosylate.
(14-2): Synthesis of trans-4-(N-Heptanoylaminomethyl)cyclohexanecarboxylic Acid Benzyl Ester:

In 40 ml of pyridine was dissolved 3.87 g of the compound obtained in step (14-1) above and after adding dropwise heptanoylchloride to the solution under ice-cooling, the mixture was stirred for 1.5 hours at room temperature.

Then, after adding 100 ml of dichloromethane to the reaction mixture, the mixture was successively washed three times each time with 30 ml of 10% hydrochloric acid, once with 30 ml of a saturated aqueous sodium hydrogen carbonate solution, and then 30 ml of a saturated aqueous sodium chloride solution and after drying with magnesium sulfate, the solvent was distilled off under reduced pressure.

Then, the crude oily product thus formed was recrystallized from a mixture of ethyl acetate and hexane (3:1 by volume) to provide 2.83 g (yield 79%) of colorless acicular trans-4-(N-heptanoylaminomethyl)cyclohexanecarboxylic acid benzyl ester.
(14-3): Synthesis of trans-4-(N-Heptylaminomethyl)cyclohexanecarboxylic Acid Benzyl Ester Hydrochloride:

To 33 ml of a tetrahydrofuran solution of 1 mol of a boran-tetrahydrofuran complex was added dropwise slowly 30 ml of a tetrahydrofuran solution of 5.4 g of the compound obtained in step (14-2) above under a nitrogen gas stream at $-20°$ C. over a period of 15 minutes.

After stirring the mixture for 30 minutes at room temperature, the mixture was refluxed for 1.5 hours. The reaction mixture obtained was ice-cooled and 10 ml of 6N hydrochloric acid was added dropwise thereto. Then, after purging hydrogen gas formed by heating, the solvent was distilled off under reduced pressure.

After adding 50 ml of ethyl acetate to the residue formed, the mixture was washed twice each time with 20 ml of purified water and after drying with magnesium sulfate, the solvent was distilled off under reduced pressure. The residue thus formed was recrystallized from diethyl ether to provide 2.0 g (yield 35%) of trans-4-(N-heptylaminomethyl)cyclohexanecarboxylic acid benzyl ester hydrochloride as a colorless powder.
(14-4): Synthesis of trans-4-(N-Heptylaminomethyl)cyclohexanecarboxylic Acid Hydrochloride:

In 10 ml of ethyl acetate was dissolved 1.14 g of the compound obtained in (14-3) above and, after adding 110 mg of palladium black and 1.5 ml of cyclohexene to the solution, the mixture was refluxed for 2.5 hours.

After cooling the reaction mixture, crystals deposited and palladium black were collected by filtration, added to methanol to dissolve the crystals, and palladium black was filtered off. The methanol solution (filtrate) was concentrated and diethyl ether was added to form crystals, which were collected to provide 525 mg (yield 60%) of colorless powdery trans-4-(N-heptylaminomethyl)cyclohexanecarboxylic acid hydrochloride.

The structure of the compound obtained was confirmed by $^1$H-NMR and IR.

(14-5): Synthesis of the Title Compound:

In 2 ml of dichloromethane were dissolved 376 mg of the compound obtained in step (14-4) above and 402 mg of the compound obtained in step (12-2) in Example 12, and after adding thereto 266 mg of DCC under ice-cooling, the reaction was carried out in the same manner as in the step (12-3) in Example 12, and the reaction product obtained was recrystallized from methanol to provide 70 mg (yield 10%) of the colorless powder of the above-described title compound.

The structure of the compound obtained was confirmed by $^1$H-NMR and IR.

EXAMPLE 15

Synthesis of
4-[trans-4'-(N-Heptylaminomethyl)cyclohexylcarbonyloxy]benzoic Acid
4''-(2-Methylbutyloxycarbonyl)phenyl Ester In 2 ml of dichloromethane were dissolved 410 mg of the compound obtained in step (14-4) in Example 14 and 642 mg of the compound obtained in step (13-1) in Example 13, and after adding thereto 291 mg of DCC under ice-cooling, the reaction was carried out in the same manner as in the step (12-3) in Example 12, and the product obtained was recrystallized from methanol to obtain 160 mg (yield 20%) of the colorless powder of the captioned title compound.

The structure of the compound obtained was confirmed by $^1$H-NMR and IR.

EXAMPLE 16

Synthesis of
trans-4-(N-Decyl-N-methylamino-ethyl)cyclohexanecarboxylic Acid
4''-(2-Methylbutyloxycarbonyl)-4'-biphenyl Ester (16-1): Synthesis of trans-4-(N-t-Butyloxycarbonylaminomethyl)cyclohexanecarboxylic Acid:

In 300 ml of a mixture of dioxane and water (2:1 by volume) was dissolved 15.7 g of tranexamic acid and 100 ml of an aqueous solution of 1 mol of sodium hydroxide and 50 ml of a dioxane solution of 24.0 g of di-t-butyl dicarbonate were added dropwise to the solution under ice-cooling over a period of 10 minutes.

After stirring the mixture for 2.5 hours at room temperature, the reaction mixture was concentrated under reduced pressure to about ⅓ of the original volume on a water bath at an external temperature of from 50° to 60° C. and then about 85 ml of 1N hydrochloric acid was added dropwise to the mixture under ice-cooling to adjust the pH thereof to from 3 to 4. The product was extracted three times, each time with 80 ml of ethyl acetate, the organic layer obtained was washed with 30 ml of purified water and then 30 ml of a saturated aqueous sodium chloride solution, and after drying with magnesium sulfate, the solvent was distilled off under reduced pressure.

The crude crystals thus formed were washed with isopropyl ether and recrystallized from ethyl acetate to provide 21.2 g (yield 82%) of colorless powdery trans-4-(N-t-butyloxycarbonylaminomethyl)cyclohexanecarboxylic acid.

(16-2): Synthesis of trans-4-(N-t-Butyloxycarbonyl-N-methylaminomethyl)cyclohexanecarboxylic Acid Methyl Ester:

In DMF were dissolved 4.1 g of the compound obtained in step (16-1) above and 8 ml of methyl iodide and while stirring the solution slowly, 1.9 g of 60% sodium hydride was added little by little to the solution under ice-cooling.

After stirring the mixture overnight at room temperature, the reaction mixture was diluted with 80 ml of diethyl ether and 5 ml of purified water was added dropwise thereto under ice-cooling. The organic layer formed was successively washed three times, each time with 20 ml of purified water, once with 20 ml of a saturated aqueous sodium hydrogen carbonate solution, and 20 ml of a saturated sodium chloride solution and after drying with magnesium sulfate, the solvent was distilled off under reduced pressure to obtain 6.8 g (yield 100%) of yellow oily crude trans-4-(N-t-butyloxycarbonyl-N-methylaminomethyl)cyclohexanecarboxylic acid methyl ester.

(16-3): Synthesis of trans-4-(N-Decyl-N-methylaminomethyl)cyclohexanecarboxylic Acid Methyl Ester:

To 6.8 g of the compound obtained in step (16-2) above was added 15 ml of an ethyl acetate solution of 4N hydrochloric acid under ice-cooling and, after stirring the mixture for 15 minutes, the solvent was distilled off under reduced pressure until an irritating odor vanished.

In 10 ml of DMF was dissolved the crude trans-4-(N-methylaminomethyl)cyclohxanecarboxylic acid methyl ester hydrochloride and then 2.2 ml of triethylamine and 4.1 ml of decyl bromide were added thereto under ice-cooling. Then after adding little by little 768 mg of 60% sodium hydride, the mixture was heated to 80° C. for from 1 to 2 hours. After cooling, the reaction mixture was diluted with 80 ml of diethyl ether and 5 ml of purified water was slowly added dropwise to the diluted mixture. The organic layer formed was collected, washed successively with 20 ml o purified water, 20 ml of a saturated aqueous sodium hydrogen carbonate solution, and 20 ml of a saturated aqueous sodium chloride solution, and after drying with magnesium sulfate, the solvent was distilled off under reduced pressure.

Then, 50 g of the yellow oily product thus obtained was applied to column chromatography using 50 g of silica gel and from the fraction of ethyl acetatehexane (1:6 by volume), 3.2 g (yield 61%) of colorless oily trans-4-(N-decyl-N-methylaminomethyl)cyclohxanecarboxylic acid methyl ester was obtained.

(16-4): Synthesis of trans-4-(N-Decyl-N-methylaminomethyl)cyclohexanecarboxylic Acid Hydrochloride:

In 6N hydrochloric acid was dissolved 3.2 g of the compound obtained in the above step (16-3) and the mixture was stirred for 24 hours at room temperature.

The solvent was distilled off under reduced pressure to provide 2.9 g (yield 86%) of colorless powdery trans 4-(N-decyl-N-methylaminomethyl)cyclohxanecarboxylic acid hydrochloride.

The structure of the compound obtained was confirmed by $^1$H-NMR and IR.

(16-5): Synthesis of the Title Compound:

In 2 ml of dichloromethane were dissolved 270 mg of the compound obtained in step (16-4) above and 221 mg of the compound obtained in step (12-2) in Example 12 and after adding thereto 160 mg of DCC and 12 mg of 4-pyrrolidinopyridine, the mixture was stirred overnight at room temperature.

Then, by processing the reaction mixture as in step (12-3) in Example 12 and recrystallizing from hexane, 70 mg (yield 16%) of the colorless powder of the above-described title compound was obtained.

The structure of the compound obtained was confirmed by $^1$H-NMR and IR.

EXAMPLES 17 TO 20

Compounds of formula (Ib) each having a different alkyl chain length shown in Table 3 below were obtained by following a similar procedure to the above procedure.

The structures of the compounds obtained were confirmed by $^1$H-NMR and IR.

EXAMPLE 21

Synthesis of trans-4-(N,N-Dimethylaminomethyl)cyclohexanecarboxylic Acid 4''-(2-Methylbutyloxy)-4'-biphenyl Ester (21-1): Synthesis of 4-(2-Methylbutyloxy)-4'-hydroxybiphenyl:

In 20 ml of ethanol was dissolved 1.86 g of 4,4'-dihydroxybiphenyl and, after adding thereto 617 mg of potassium hydroxide and 1.31 ml of benzyl bromide, the mixture was refluxed for 6 hours.

After cooling, the crystals deposited were collected by filtration, dissolved in hot acetone, and insoluble mater was filtered off.

Then, the solvent of the acetone layer (filtrate) was distilled off under reduced pressure to provide 1.37 g (yield 50%) of colorless powdery 4-bezyloxy-4'-hydroxybiphenyl.

In 3 ml of DMF was dissolved 319 mg of 4-benzyloxy-4'-hydroxybiphenyl and after adding thereto 148 mg of potassium hydroxide and 319 mg of p-toluenesulfonic acid 2-methylbutyl ester, the mixture was stirred for 4 hours at 50° C.

After cooling, 30 ml of ethyl acetate was added to the reaction mixture, the organic layer formed was collected, successively washed twice each time with 10 ml of purified water, once with 10 ml of 10% hydrochloric acid, 10 ml of a saturated aqueous sodium hydrogen carbonate solution, and 30 ml of a saturated sodium chloride solution, and dried with magnesium sulfate. Then, the solvent was distilled off under reduced pressure and the product was recrystallized from ethanol to provide 450 mg (yield 99%) of colorless powdery 4-benzyloxy-4'-(2-methylbutyloxy)biphenyl.

In 3 ml of ethanol was dissolved 265 mg of 4-benzyloxy-4'-(2-methylbutyloxy)biphenyl and after adding thereto 13 mg of palladium black and 0.4 ml of cyclohexene, the mixture was refluxed for one hour.

Then, palladium black was filtered off and the filtrate was concentrated to obtain 192 mg (yield 98%) of colorless powdery 4-(2-methylbutyloxy)-4'-hydroxybiphenyl.

(21-2): Synthesis of the Title Compound:

In 3 ml of carbon tetrachloride was dissolved 177 mg of the compound obtained in step (12-1) in Example 12 and, after adding dropwise 0.3 ml of thionyl chloride and one drop of DMF to the solution, the mixture was refluxed for 1.5 hours. The solvent was distilled off under reduced pressure and the residue was dissolved in 3 ml of toluene. The solution was added dropwise to 2 ml of a pyridine solution of 192 mg of the compound obtained in the above step (21-1) under ice-cooling and then the mixture was refluxed for one hour.

After cooling, 30 ml of ethyl acetate was added to the reaction mixture, the mixture was washed three times, each time with 10 ml of purified water and once with 10 ml of a saturated aqueous sodium chloride solution and dried with magnesium sulfate. The solvent was distilled off under reduced pressure, crude crystals thus obtained were applied to column chromatography using 8 g of silica gel, and the fraction of 3% methanol-methylene chloride was concentrated and recrystallized from methanol to obtain 151 mg (yield 48%) of the colorless acicular above-described title compound.

The structures of the compound obtained was confirmed by $^1$H-NMR and IR.

EXAMPLE 22

Synthesis of 4-[trans-4'-(N,N-Dimethylaminomethyl)cyclohexylcarbonyloxy]benzoic Acid 4''-(2-Methylbutyloxy)-phenyl Ester (22-1): Synthesis of 4-(2-Methylbutyloxy)phenol:

In 20 mg of DMF was dissolved 400 g of hydroquinone monobenzyl ether and after adding thereto 3.36 g of pulverized potassium hydroxide and 4.84 g of p-toluenesulfonic acid 2-methylbutyl ester, the mixture was stirred for 3 hours at room temperature.

The reaction mixture was diluted with 50 ml of ethyl acetate, washed twice each time with 30 ml of purified water, once with 30 ml of 10% hydrochloric acid, 30 ml of a saturated aqueous sodium hydrogen carbonate solution, and 30 ml of a saturated aqueous sodium chloride solution and after drying with magnesium sulfate, the solvent was distilled under reduced pressure.

The crude crystals obtained were column chromatographed using 55 g of silica gel and from the fraction of 2% ethyl acetate-hexane, 4.31 g (yield 64%) of colorless powdery 4-(2-methylbutyloxy)phenylbenzyl ether was obtained.

In 30 ml of ethanol was dissolved 4.31 g of the 4-(2-methylbutyloxy)phenylbenzyl ether thus obtained and after adding thereto 216 mg of palladium black and 8 ml of cyclohexene, the mixture was refluxed for one hour. After cooling, palladium black was filtered off and the solvent was distilled off from the filtrate under reduced pressure to obtain 3.03 g (yield 68%) of colorless oily 4-(2-methylbutyloxy)phenol.

(22-2): Synthesis of 4-Hydroxybenzoic Acid 4'-(2-Methylbutyloxy)phenyl Ester:

In 10 ml of carbon tetrachloride was dissolved 616 mg of 4-benzyloxybenzoic acid and after adding 1.0 g of thionyl chloride and one drop of DMF to the solution, the mixture was refluxed for 2.5 hours.

The solvent was distilled off from the reaction mixture and the residue was dissolved in 5 ml of toluene. The solution was added dropwise to 10 ml of a toluene-pyrridine mixture (4:1 by volume) containing 450 mg of 4-(2-methylbutyloxy)phenol under ice-cooling, and the mixture was refluxed for one hour.

After cooling, the reaction mixture was diluted with 30 ml of ethyl acetate, washed twice each time with 10 ml of purified water, once with 10 ml of 10% hydrochloric acid, 10 ml of a saturated aqueous sodium hydrogen carbonate solution, and 10 ml of a saturated aqueous sodium chloride solution, and dried with magnesium sulfate.

The solvent was distilled off under reduced pressure from the reaction mixture and the residue was recrystallized from ethanol to obtain 605 mg (yield 57%) of colorless flaky crystals of 4-benzyloxybenzoic acid 4'-(2-methylbutyloxy)phenylester.

In 5 ml of ethanol was dissolved 560 mg of the ester obtained and after adding thereto 28 mg of palladium black and 0.73 ml of cyclohexene, the resultant mixture was refluxed for one hour. The reaction mixture was filtered, the solvent was distilled off from the filtrate under reduced pressure and the residue was recrystallized from methanol to obtain 430 mg (yield 99%) of colorless acicular 4-hydroxybenzoic acid 4'-(2-methylbutyloxy)phenylester.

(22-3): Synthesis of the Title Compound:

After esterifying 333 mg of the compound obtained in the step (12-1) in Example 12 and 300 mg of the compound obtained in step (22-2) above in the same manner as in step (21-2) in Example 21 using 0.63 mg of thionyl chloride, the product was recrystallized from hexane to provide 149 mg (yield 32%) of the colorless acicular above-described title compound.

The structures of the compound obtained was confirmed by $^1$H-NMR and IR.

EXAMPLES 23 to 26

By following the same procedure as in Example 16, compounds of Examples 23 to 26 of formula (Ib) wherein $R_1''$ had a group with optical activity were obtained. These compounds are shown in Table 3 below.

The structures of the compounds obtained were confirmed by $^1$H-NMR and IR.

In addition, the phase transition temperatures of the compounds of Examples 12 to 26 were measured and the results obtained are shown in Table 3 below.

Also, the IR and $^1$H-NMR of the compounds of Examples 12 to 26 and the intermediates in Examples 12, 14, 16 and 23 were measured and the results are shown in Table 4 and Table 5 below.

Also, the spontaneous polarization of the compounds of Examples 12 to 26, was measured for compounds showing chiralsmectic C phase and the results obtained are shown in Table 3 below.

The spontaneous polarization was measured by the method shown in Example 1.

TABLE 3

$$R_1'' \text{—} \phenyl \text{—}(COO)_n\text{—} \phenyl \text{—} Y\text{—} R_3''$$

| Example No. | R1″ | R2 | Y—R3″ structure | Phase Transition Temperature Cry—Sx—Sc*—S_A—Ch—Iso (°C.) | | | | | | Spontaneous Polarization (nC/cm²) |
|---|---|---|---|---|---|---|---|---|---|---|
| 12 | —CH₃ | —CH₃ | biphenyl-COOCH₂CH(CH₃)C₂H₅ | •45 | •64 | •92 | | | • | — |
| 13 | —CH₃ | —CH₃ | phenyl-COO-phenyl-COOCH₂CH(CH₃)C₂H₅ | •60 | | •114 | •127 | | • | — |
| 14 | —C₇H₁₅ | H | biphenyl-COOCH₂CH(CH₃)C₂H₅ | •37 | | •134 | | | • | — |
| 15 | —C₇H₁₅ | H | phenyl-COO-phenyl-COOCH₂CH(CH₃)C₂H₅ | •62 | | •130 | | | • | — |
| 16 | —C₁₀H₂₁ | —CH₃ | biphenyl-COOCH₂CH(CH₃)C₂H₅ | •40 | | •53 | | | • | — |
| 17 | —C₁₀H₂₁ | H | phenyl-COO-phenyl-COOCH₂CH(CH₃)C₂H₅ | •35 | | •138 | | | • | — |
| 18 | —C₅H₁₁ | —CH₃ | phenyl-COO-phenyl-COOCH₂CH(CH₃)C₂H₅ | •54 | | •66 | | | • | — |
| 19 | —CH₃ | —CH₃ | phenyl-COO-phenyl-COO—CH(CH₃)C₆H₁₃ | •52 | •60 | •89 | | | • | — |

TABLE 3-continued

Structure: ⬡—(COO)ₙ—⬡—Y—R₃″

| Example No. | R1″ | R2 | Y—R₃″ (structure) | Phase Transition Temperature Cry—Sx—Sc*—S_A—Ch—Iso (°C.) | | | | | | Spontaneous Polarization (nC/cm²) |
|---|---|---|---|---|---|---|---|---|---|---|
| 20 | —CH₃ | —CH₃ | ⬡—COO—⬡—COO—CH(CH₃)C₃H₇ | •47 | •52 | | •100 | | • | — |
| 21 | —CH₃ | —CH₃ | ⬡—⬡—OCH₂CH(CH₃)C₂H₅ | •107 | •114 | | | •118 | •120 • | — |
| 22 | —CH₃ | —CH₃ | ⬡—COO—⬡—OCH₂CH(CH₃)C₂H₅ | •110 | | | | | •128 • | — |
| 23 | C₂H₅*CH(CH₃)CH₂— | —CH₃ | ⬡—⬡—COOC₇H₁₅ | •27 | •40 | •52 | | | • | 0.1 |
| 24 | C₂H₅*CH(CH₃)CH₂— | —CH₃ | ⬡—⬡—OC₇H₁₅ | •<r.t. | •98 | •119 | | | •125 • | 1.5 |
| 25 | C₂H₅*CH(CH₃)CH₂— | —CH₃ | ⬡—⬡—OC₈H₁₇ | •40 | •95 | •121 | | | •125 • | 2.9 |
| 26 | C₂H₅*CH(CH₃)CH₂— | —CH₃ | ⬡—⬡—OC₁₂H₂₅ | •<r.t. | •78 | •118 | | | • | 2.1 |

(Note)
The term "r.t." means room temperature and has hereafter the same meaning.

TABLE 4

| Example No. | IR Spectrum (cm$^{-1}$) | $^1$H-NMR Spectrum (ppm) |
|---|---|---|
| 12 | 2810 | 0.97 |
|  | 2765 | 1.03 |
|  | 2730 | 1.10–2.03 |
|  | 1755 | 2.17 |
|  | 1710 | 2.28 |
|  | 1605 | 2.43–2.63 |
|  | 1490 | 4.11–4.29 |
|  |  | 7.17 |
|  |  | 7.63 |
|  |  | 7.64 |
|  |  | 8.10 |
| 13 | 2810 | 0.97 |
|  | 2765 | 1.03 |
|  | 2730 | 1.20–2.23 |
|  | 1755 | 2.11 |
|  | 1740 | 2.23 |
|  | 1710 | 2.49 |
|  | 1600 | 2.49–2.66 |
|  | 1500 | 4.11–4.29 |
|  |  | 7.26 |
|  |  | 7.31 |
|  |  | 8.14 |
|  |  | 8.26 |
| 14 | 2800 | 0.89 |
|  | 1745 | 0.97 |
|  | 1710 | 1.03 |
|  | 1605 | 0.85–2.60 |
|  | 1490 | 2.50 |
|  |  | 2.60 |
|  |  | 3.28–3.77 |
|  |  | 4.11–4.31 |
|  |  | 7.1 |
|  |  | 7.63 |
|  |  | 7.66 |
|  |  | 8.11 |
| 15 | 2800 | 0.86 |
|  | 1760 | 0.97 |
|  | 1735 | 1.03 |
|  | 1720 | 1.09–2.66 |
|  | 1600 | 2.60 |
|  | 1510 | 2.70 |
|  |  | 3.26–3.49 |
|  |  | 4.11–4.29 |
|  |  | 7.2 |
|  |  | 7.29 |
|  |  | 8.11 |
|  |  | 8.20 |
| 16 | 2775 | 0.86 |
|  | 1755 | 0.97 |
|  | 1720 | 1.03 |
|  | 1605 | 0.83–2.37 |
|  | 1490 | 2.14 |
|  |  | 2.20 |
|  |  | 2.31 |
|  |  | 2.43–2.63 |
|  |  | 4.11–4.31 |
|  |  | 7.17 |
|  |  | 7.63 |
|  |  | 7.66 |
|  |  | 8.11 |
| 17 | 2800 | 0.86 |
|  | 1760 | 0.94 |
|  | 1735 | 1.00 |
|  | 1720 | 0.86–2.66 |
|  | 1600 | 2.51 |
|  | 1500 | 2.60 |
|  |  | 2.66–2.82 |
|  |  | 4.08–4.26 |
|  |  | 7.23 |
|  |  | 7.29 |
|  |  | 8.14 |
|  |  | 8.23 |
| 18 | 2775 | 0.91 |
|  | 1755 | 0.97 |
|  | 1720 | 1.03 |
|  | 1605 | 0.97–2.37 |
|  | 1490 | 2.20 |
|  |  | 2.23 |
|  |  | 2.34 |
|  |  | 2.42–2.77 |
|  |  | 4.08–4.31 |
|  |  | 7.17 |
|  |  | 7.63 |
|  |  | 7.66 |
|  |  | 8.11 |
| 19 | 2810 | 0.88 |
|  | 2765 | 0.88–1.48 |
|  | 2730 | 1.36 |
|  | 1750 | 1.48–2.20 |
|  | 1735 | 2.11 |
|  | 1720 | 2.23 |
|  | 1600 | 2.46–2.66 |
|  | 1500 | 5.11–5.27 |
|  |  | 7.26 |
|  |  | 7.29 |
|  |  | 8.14 |
|  |  | 8.23 |
| 20 | 2810 | 0.96 |
|  | 2775 | 0.88–1.14 |
|  | 2730 | 1.36 |
|  | 1750 | 1.32–2.28 |
|  | 1735 | 2.12 |
|  | 1715 | 2.23 |
|  | 1600 | 2.49–2.66 |
|  | 1500 | 5.11–5.29 |
|  |  | 7.24 |
|  |  | 7.31 |
|  |  | 8.14 |
|  |  | 8.23 |
| 21 | 2810 | 0.96 |
|  | 2765 | 1.03 |
|  | 2730 | 1.17–2.29 |
|  | 1755 | 2.14 |
|  | 1605 | 2.26 |
|  | 1490 | 2.46–2.61 |
|  | 1250 | 3.70–3.90 |
|  |  | 6.97 |
|  |  | 7.11 |
|  |  | 7.49 |
|  |  | 7.54 |
| 22 | 2810 | 0.96 |
|  | 2765 | 1.03 |
|  | 2730 | 0.88–2.31 |
|  | 1760 | 2.11 |
|  | 1740 | 2.23 |
|  | 1605 | 2.46–2.63 |
|  | 1505 | 3.70–3.85 |
|  | 1250 | 6.94 |
|  |  | 7.11 |
|  |  | 7.23 |
|  |  | 8.23 |
| 23 | 2775 | 0.86 |
|  | 1755 | 0.89 |
|  | 1720 | 0.91 |
|  | 1605 | 0.86–2.23 |
|  | 1490 | 2.16 |
|  |  | 2.43–2.63 |
|  |  | 4.34 |
|  |  | 7.17 |
|  |  | 7.62 |
|  |  | 7.63 |
|  |  | 8.10 |
| 24 | 2810 | 0.86 |
|  | 2765 | 0.89 |
|  | 2730 | 0.91 |
|  | 1755 | 0.74–2.28 |
|  | 1605 | 2.16 |
|  | 1490 | 2.43–2.63 |
|  | 1250 | 3.97 |
|  |  | 6.97 |
|  |  | 7.14 |
|  |  | 7.49 |
|  |  | 7.54 |
| 25 | 2810 | 0.86 |
|  | 2765 | 0.89 |
|  | 2730 | 0.91 |
|  | 1755 | 0.74–2.28 |
|  | 1605 | 2.16 |

TABLE 4-continued

| Example No. | IR Spectrum (cm$^{-1}$) | $^1$H-NMR Spectrum (ppm) |
|---|---|---|
|  | 1490 | 2.43–2.63 |
|  | 1250 | 3.97 |
|  |  | 6.97 |
|  |  | 7.14 |
|  |  | 7.49 |
|  |  | 7.54 |
| 26 | 2810 | 0.86 |
|  | 2765 | 0.89 |
|  | 2730 | 0.91 |
|  | 1755 | 0.86–2.23 |
|  | 1605 | 2.11 |
|  | 1490 | 2.37–2.60 |
|  | 1250 | 3.97 |
|  |  | 6.94 |
|  |  | 7.09 |
|  |  | 7.46 |
|  |  | 7.51 |

TABLE 5

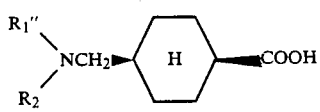

| Example No. | R$_1$" | R$_2$ | IR Spectrum (cm$^{-1}$) | $^1$H-NMR Spectrum (ppm) |
|---|---|---|---|---|
| 12 | —CH$_3$ | —CH$_3$ | 3330 | 0.97–1.60 |
|  |  |  | 2650 | 1.71–2.11 |
|  |  |  | 1700 | 2.18–2.35 |
|  |  |  |  | 2.90 |
|  |  |  |  | 3.03 |
| 14 | —C$_{17}$H$_{15}$ | H | 3420 | 0.91 |
|  |  |  | 2780 | 1.00–2.42 |
|  |  |  | 1600 | 2.89 |
|  |  |  | 1700 | 3.00 |
| 16 | —C$_{10}$H$_{21}$ | —CH$_3$ | 3330 | 0.86 |
|  |  |  | 2650 | 0.91–2.37 |
|  |  |  | 1700 | 2.80 |
|  |  |  |  | 2.80–3.20 |
| 23 | * C$_2$H$_5$CHCH$_2$— <br> \| <br> CH$_3$ | —CH$_3$ | 3330 | 0.96 |
|  |  |  | 2650 | 0.98 |
|  |  |  | 1700 | 1.03–1.77 |
|  |  |  |  | 1.80–2.38 |
|  |  |  |  | 2.86 |
|  |  |  |  | 2.75–3.08 |

As is clear from the above results, the compounds of this invention shown by formula (Ib) exhibit a liquid crystal phase over a wide temperature range near room temperature. Thus, the invention provides simply and at low cost, novel liquid crystal compounds useful as a thermal-writing liquid crystal element and a liquid crystal element for display utilizing a thermooptic effect in a practical temperature range, alone or as an appropriate mixture with other smectic liquid crystals.

EXAMPLES 27 TO 35

Synthesis of trans-4-(N-Methyl-N-(S)-2-methylbutylaminomethyl)-cyclohexanecarboxylic Acid Ester After adding 1 equivalent of DCC and 0.1 equivalent of 4-pyrrolidinopyridine to the trans-4-(N-methyl-N-(S)-2-methylbutylaminomethyl)cyclohexanecarboxylic acid produced in a similar manner to that in Example 16 and the phenol derivative shown in Table 6 below produced in a similar manner to that in step (13-1), (22-1) or (22-2) in dichloromethane, the mixture was stirred overnight. After post-treatment, the product was recrystallized from hexane to obtain each of the compounds shown by the following formula

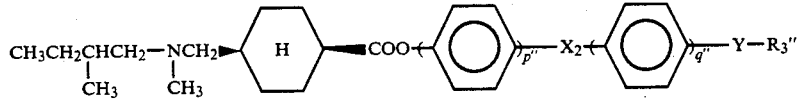

as compounds of Examples 27 to 35. The yields of these compounds were from 20% to 50%.

The phase transition temperatures of these compounds were measured and the results are shown in Table 6 below.

Furthermore, the structures of the compounds obtained were confirmed by $^1$H-NMR and IR. The results obtained are shown in Table 7 below.

TABLE 6

| Example No. | ![structure] | Phase Transition Temperature Cry—Sx—Sc*—S$_A$—Ch—Iso |
|---|---|---|
| 27 | -⟨O⟩-CO-O-⟨O⟩-⟨O⟩-CO-C$_7$H$_{15}$ (with C=O groups) | •39  •150    •174 •195 • |
| 28 | -⟨O⟩-CO-O-⟨O⟩-⟨O⟩-O-C$_7$H$_{15}$ | •80  •161         •218 • |

TABLE 6-continued $+\bigcirc-\!\!{}_{p''}\!\!-\!X_2\!+\!\bigcirc-\!\!{}_{q'''}\!\!-Y-R_3''$

| Example No. | Structure | Phase Transition Temperature Cry—Sx—Sc*—S$_A$—Ch—Iso |
|---|---|---|
| 29 | –⟨Ph⟩–CO–O–⟨Ph⟩–⟨Ph⟩–O–C$_{12}$H$_{25}$ | •r.t. •90 •165 •197 • |
| 30 | –⟨Ph⟩–⟨Ph⟩–CO–O–⟨Ph⟩–CO–C$_7$H$_{15}$ | •r.t. •85 •217 • |
| 31 | –⟨Ph⟩–⟨Ph⟩–CO–O–⟨Ph⟩–O–C$_7$H$_{15}$ | •r.t. •215 •244 • |
| 32 | –⟨Ph⟩–⟨Ph⟩–O–CO–⟨Ph⟩–O–C$_5$H$_{11}$ | •r.t. •143 •157 •233 • |
| 33 | –⟨Ph⟩–⟨Ph⟩–O–CO–⟨Ph⟩–O–C$_7$H$_{15}$ | •r.t. •145 •186 •233 • |
| 34 | –⟨Ph⟩–⟨Ph⟩–O–CO–⟨Ph⟩–O–C$_{10}$H$_{21}$ | •r.t. •132 •192 •222 • |
| 35 | –⟨Ph⟩–⟨Ph⟩–O–CO–⟨Ph⟩–O–C$_{12}$H$_{25}$ | •r.t. •120 •175 •215 • |

TABLE 7

| Example No. | IR Spectrum (cm$^{-1}$) | NMR Spectrum (ppm) |
|---|---|---|
| 27 | 2795, 2770, 1760, 1730, 1710, 1605, 1500, 1495 | 0.86, 0.87, 0.94–1.89, 1.90–2.29, 2.14, 2.46–2.63, 4.36, 7.26, 7.34, 7.67, 7.70, 8.14, 8.25 |
| 28–29 | 2795, 2775, 1755, 1740, 1605, 1500 | 0.86, 0.87, 0.94–1.90*$^3$, 1.91–2.26, 2.16, 2.43–2.63, 4.01, 6.99, 7.24, 7.26, 7.53, 7.60, 8.27 |
| 30 | 2795, 2770, 1760, 1740, 1720, 1605, 1505, 1495 | 0.86, 0.87, 0.91–1.86, 1.86–2.26, 2.13, 2.43–2.61, 4.31, 7.19, 7.31, 7.66, 7.71, 8.13, 8.27 |
| 31 | 2795, 2770, 1755, 1740, 1605, 1510, 1495 | 0.89, 0.87, 0.97–1.86, 1.91–2.36, 2.41–2.61, 3.96, 6.93, 7.13, 7.17, 7.66, 7.70, 8.24 |
| 32–35 | 2795, 2770, 1750, 1730, 1605, 1510, 1495 | 0.86, 0.87, 0.94–1.89*$^3$, 1.90–2.24, 2.14, 2.40–2.60, 4.04, 6.97, 7.14, 7.27, 7.57, 7.60, 8.14 |

(Note)
*$^3$The peak height varied depending on the chain length of alkylene groups in the compounds, respectively.

In the above examples, only examples using S-substances as the optically active substances were used as the starting materials. However, it is clear from a theoretical view point that when R-substances are used as the starting materials, products having the same phase transition temperature as in using the S-substance are obtained.

As is clear from the above results, the compounds of this invention shown by formula (Ic) have a ferroelectric characteristics over a very wide temperature range and the invention can provide, simply and at low cost, novel compounds useful as materials for a liquid crystal display elements using an electrooptic effect in a practical temperature range, alone or as an appropriate mixture with other nematic, smectic, or ferroelectric liquic crystals.

EXAMPLE 36

Synthesis of 4-Octyloxy-4'-biphenylcarboxylic Acid trans-4''-(N-(S)-2-methylbutyl-N-methylamino)cyclohexyl Ester (36-1): Synthesis of trans-4-N-t-butyloxycarbonylaminocyclohexanol:

In 90 ml of a mixture of dioxane and water (2:1 by volume) was dissolved 4.7 g of commercially available trans-4-aminocyclohexanol hydrochloride, and 60 ml of 1M sodium hydroxide aqueous solution and 7.9 g of di-t-butyl dicarbonate were added dropwise thereto under ice-cooling over a period of 10 minutes. Then, after stirring the mixture for 2 hours at room temperature, the reaction mixture was concentrated under reduced pressure to about ⅓ of the original volume on a water both at an external temperature of from 50° to 60° C.

The reaction mixture was extracted three times each time with 30 ml of ethyl acetate, and the organic layer was washed with 30 ml of purified water and 30 ml of a saturated aqueous sodium chloride solution, and, after drying with magnesium sulfate, the solvent was distilled off under reduced pressure.

The thus obtained crude crystals was recrystallized from ethyl acetate to provide 6.15 g (yield 95%) of colorless acicular trans-4-N-t-butyloxycarbonylaminoaminocyclohexanol.

(36-2): Synthesis of trans-4-N-t-Butyloxycarbonylaminocyclohexylbenzyl Ether:

To 100 ml of tetrahydrofuran was suspended 2.2 g of 60% sodium hydride under ice-cooling, and 5.4 g of the compound obtained in step (36-1) above was added thereto. Then, 3.3 ml of benzyl bromide was added dropwise to the mixture and the temperature of the reaction mixture was gradually increased to room temperature. Thereafter, the reaction mixture was heated at a temperature of 50° to 60° C. for 1 hour.

After cooling, 10 ml of purified water was added to the reaction mixture, which was then concentrated. 200 ml of hexane was added to the concentrated mixture, insoluble crystals were removed, and the solvent of the separated organic layer was distilled off under reduced pressure.

The crude crystals obtained were recrystallized from hexane to provide 2.3 g (yield 35%) of colorless powdery trans-4-t-butyloxycarbonylaminocyclohexylbenzyl ether.

(36-3): Synthesis of trans-4-[N-(S)-2-Methylbutyl-N-methylamino]cyclohexylbenzyl Ether:

In 30 ml of DMF were dissolved 3 g of the compound obtained in step (36-2) above and 0.9 ml of methyl iodide, and 520 mg of 60% sodium hydride was slowly added thereto under ice-cooling.

After stirring the reaction mixture overnight at room temperature, the reaction mixture was diluted with 50 ml of diethyl ether, followed by dropwise addition of 5 ml of purified water under ice-cooling. The resulting organic layer was washed with water, and the solvent was distilled off under reduced pressure, whereby 3.6 g of a yellow oily crude product, trans-4-(N-t-butyloxycarbonyl-N-methylamino)cyclohexylbenzyl ether was obtained.

To 3.6 g of the crude oily product wad added 8 ml of an ethyl acetate solution of 4N hydrochloric acid under ice-cooling. After stirring for 30 minutes, the reaction mixture was filtered to obtain a crystal which was then dissolved in 30 ml of methylene chloride and neutralized with 10 ml of a saturated sodium hydrogen carbonate aqueous solution. The solvent of the resulting organic layer was distilled off under reduced pressure to provide 1.8 g (yield 75%) of colorless oily trans-4-N-methylaminocyclohexylbenzyl ether.

In 10 ml of DMF was dissolved 1.8 g of the thus obtained oily product, and 485 mg of 60% sodium hydride was added thereto under ice-cooling. After adding 1.3 mol of (S)-2-methylbutyl bromide dropwise thereto, the reaction mixture was heated at 60° C. for about 3 hours. Then, the reaction mixture was cooled and diluted with 50 ml of diethyl ether, to which 5 ml of purified water was dropwise added. The resulting organic layer was washed with water and the solvent was distilled off under reduced pressure to obtain a yellow oily product.

The oily product was column chromatographed using 50 g of silica gel and the fraction of 2% methyanolmethylene chloride was concentrated and recrystallized to obtained 1.3 g (yield 57%) of colorless oily trans-4-[N-(S)-2-methylbutyl-N-methylamino]cyclohexyl-benzyl ether.

(36-4): Synthesis of the Title Compound:

The compound obtained in step (36-3) above was subjected to hydrogenolysis in ethanol using palladium black and cyclohexene to convert into colorless oily trans-4-[N-(S)-2-methylbutyl-N-methylamino]cyclohexanol, which was then subjected to esterification reaction with 4-ocyloxy-4'-biphenylcarboxylic acid using thionyl chloride. The resulting product was purified with silica gel-column chromatography and recrystallized from methanol to provide a colorless powdery title compound having the following formula at the yield of about 30%.

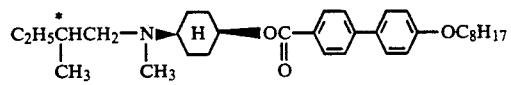

The structure of the compound obtained was confirmed by ¹H-NMR and IR, and the results are shown in Table 8. The compound had a spontaneous polorization of 7.2 nC/cm² and exhibited the following phase transition temperature:

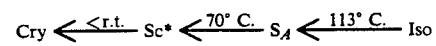

TABLE 8

| IR Spectrum (cm⁻¹) | ¹H-NMR Spectrum (ppm) |
|---|---|
| 2795 | 0.89 |
| 1710 | 0.80–1.95 |
| 1605 | 2.05–2.50 |
| 1500 | 2.26 |
|  | 4.00 |
|  | 4.82–5.00 |
|  | 6.98 |
|  | 7.57 |
|  | 7.66 |
|  | 8.06 |

EXAMPLE 37

Synthesis of 4-[N-(S)-2-Methylbutyl-N-methylamino]-cyclohexanecarboxylic Acid 4'-Octyloxy-4"-biphenyl Ester The compound obtained in step (10-1) above was subjected to necleus-hydrogenation using metallic sodium and isoamyl alcohol in the manner as described in *J.A.C.S.*, 68, 1648 (1946). The resulting product was purified with silica gel-column chromatography to isolate trans-4-[N-(S)-2-methylbutyl-N-methyl-amino]cyclohexanecarboxylic acid, which was then subjected to esterification reaction with 4-octyloxy-4'-hydroxybiphenyl using thionyl chloride.

The thus obtained product was purified with silica gel-column chromatography and recrystallized from methanol to provide a colorless powder title compound having the following formula at the yield of about 20%.

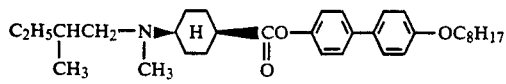

The structure of the compound obtained was confirmed by 1H-NMR and IR.

While the invention has been described in detail and with reference to specific embodiments thereof, it will be apparent to one skilled in the art that various changes and modifications can be made therein without departing from the spirit and scope thereof.

What is claimed is:

1. An amine derivative represented by formula (I)

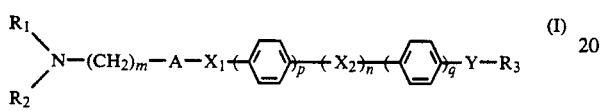

wherein A represents

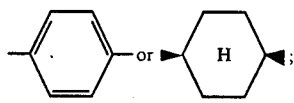

$X_1$ and $X_2$, which may be the same or different, each represents

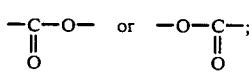

Y represents —O— or

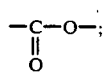

$R_1$ and $R_3$, which may be the same or different, each represents a straight chain or branched chain alkyl group having 1 to 18 carbon atoms; $R_2$ represents a hydrogen atom or a methyl group; m and n each represents 0 or 1; and p and q each represents 1 or 2, provided that p and q are 1 when n is 0, and p and q are not 2 at the same time when n is 1.

2. An amine derivative as in claim 1, represented by one of formulae (II), (III) and (IV)

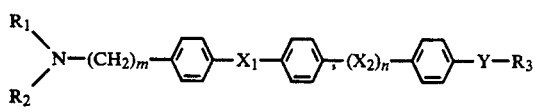

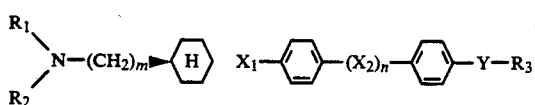

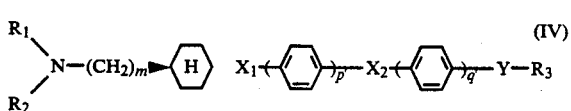

wherein $X_1$, $X_2$, Y, $R_1$, $R_2$, $R_3$, m and n are the same as those in formula (I), and p' and q' each represents 1 or 2, provided that p' and q' are not the same.

3. An amine derivative represented by formula (Ia)

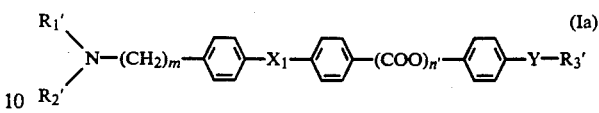

wherein $R_1'$ represents an alkyl group having from 1 to 12 carbon atoms; $R_2'$ is a methyl group; $R_3'$ represents a straight chain alkyl group having 1 to 18 carbon atoms; n' is 0 or 1; $X_1$ represents

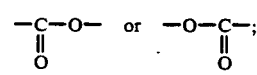

Y represents —O— or

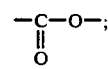

and m represents 0 or 1.

4. An amine derivative as in claim 3, wherein said n' is 0.

5. An amine as derivative in claim 1, represented by formula (Ib)

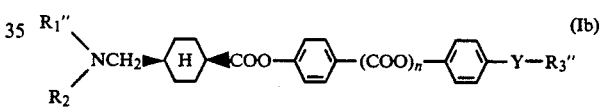

wherein $R_1''$ and $R_3''$, which may be the same or different, each represents an alkyl group having from 1 to 16 carbon atoms; and $R_2$, Y and n have same meanings as defined in claim 1.

6. An amine derivative as in claim 1, represented by formula (Ic)

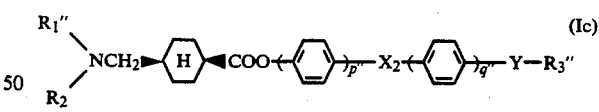

wherein $R_1''$ and $R_3''$, which may be the same or different, each represents an alkyl group having from 1 to 16 carbon atoms; p" and q" each represents 1 or 2, provided that p" and q" are not the same; and $R_2$, $X_2$, and Y have the same meanings as defined in claim 1.

7. A process for producing an amine derivative represented by formula (I)

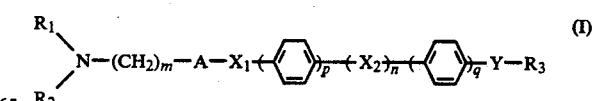

which comprises esterifying a compound of formula (V) with a compound of formula (VI):

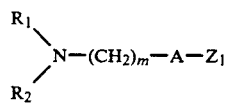 (V)

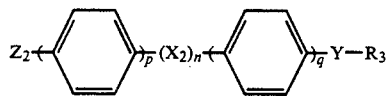 (VI)

wherein A, $X_2$, Y, $R_1$, $R_2$, $R_3$, m, n, p and q have the same meanings as defined in claim 1, and $Z_1$ and $Z_2$ represent —COOH and —OH, respectively, or vice versa.

8. A process as in claim 7, wherein said $X_1$ in formula (I) is

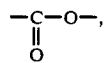

said $Z_1$ in formula (V) is —COOH, and said $Z_2$ in formula (VI) is —OH.

9. A process as in claim 7, wherein said $X_1$ in formula (I) is

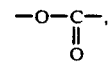

said $Z_1$ in formula (V) is —OH, and said $Z_2$ in formula (VI) is —COOH.

10. An amine derivative as in claim 1, which is a compound having the following structure:

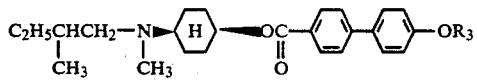

wherein $R_3$ is the same as in formula (I).

11. An amine derivative as in claim 1, which is a compound having the following structure:

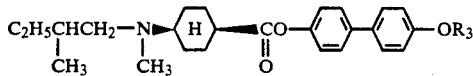

wherein $R_3$ is the same as in formula (I).

* * * * *